(12) United States Patent
Gonsky

(10) Patent No.: US 12,383,388 B2
(45) Date of Patent: Aug. 12, 2025

(54) DENTAL AEROSOL PROTECTION SYSTEM

(71) Applicant: Aerosol Control Company, Stroudsburg, PA (US)

(72) Inventor: Michael E. Gonsky, Stroudsburg, PA (US)

(73) Assignee: Aerosol Control Company, Stroudsburg, PA (US)

(*) Notice: Subject to any disclaimer, the term of this patent is extended or adjusted under 35 U.S.C. 154(b) by 1015 days.

(21) Appl. No.: 17/337,051

(22) Filed: Jun. 2, 2021

(65) Prior Publication Data

US 2021/0369433 A1   Dec. 2, 2021

Related U.S. Application Data

(60) Provisional application No. 63/033,808, filed on Jun. 2, 2020, provisional application No. 63/033,805, filed on Jun. 2, 2020.

(51) Int. Cl.
  *A61C 19/00*   (2006.01)
  *A61B 90/00*   (2016.01)
  (Continued)

(52) U.S. Cl.
  CPC ............. *A61C 19/00* (2013.01); *A61B 90/05* (2016.02); *A61B 90/40* (2016.02); *A61M 16/06* (2013.01)

(58) Field of Classification Search
  CPC ..................... A41D 13/11; A41D 13/1184; A61B 2218/00; A61B 2218/001;
  (Continued)

(56) References Cited

U.S. PATENT DOCUMENTS

| 3,747,599 A | 7/1973 | Malmin |
| 4,764,990 A * | 8/1988 | Markert ............... A61F 9/02 128/201.15 |

(Continued)

FOREIGN PATENT DOCUMENTS

| CN | 111281321 A | 6/2020 |
| IN | 202041051154 A | 4/2020 |

OTHER PUBLICATIONS

International Appln. No. PCT/US2021/035485—International Search Report and Written Opinion of the International Searching Authority, dated Sep. 21, 2021, 40 pages.

*Primary Examiner* — Elliot S Ruddie
(74) *Attorney, Agent, or Firm* — Clinton H. Wilkinson; Wilkinson Law Office

(57) ABSTRACT

A dental aerosol protection system for controlling dispersion of aerosol and splatter particles produced during dental procedures, the system including a ring assembly, a support mask for supporting the ring assembly on a patient, and a suction generating device, the ring assembly and support mask having suction ports which are connectable to the suction generating device to provide a negative suction force around the oral cavity, wherein the ring assembly and support mask can be connected or used separately to control dispersion of aerosols depending upon the requirements of the dental procedure, and one or more flexible extensions connectable to the ring assembly and support mask extending superiorly away from the patient around and over the oral cavity, the flexible extensions forming an adjustable physical barrier between the dental professional and the patient's oral cavity.

20 Claims, 14 Drawing Sheets

(51) Int. Cl.
*A61B 90/40* (2016.01)
*A61M 16/06* (2006.01)

(58) Field of Classification Search
CPC ........ A61B 2218/007; A61B 2218/008; A61B 90/05; A61B 90/40; A61B 2090/401; A61C 17/06; A61C 19/00; A61C 17/08; A61C 17/12; A61M 16/06–0694
See application file for complete search history.

(56) References Cited

U.S. PATENT DOCUMENTS

| | | | |
|---|---|---|---|
| 9,827,723 B2 | 11/2017 | Klockseth | |
| 10,952,812 B1* | 3/2021 | Saadat | A61B 90/40 |
| 2014/0366890 A1* | 12/2014 | Tao | A61M 16/009 |
| | | | 128/849 |
| 2017/0173371 A1 | 6/2017 | Truex et al. | |
| 2018/0132550 A1* | 5/2018 | Czajka | A62B 18/045 |

* cited by examiner

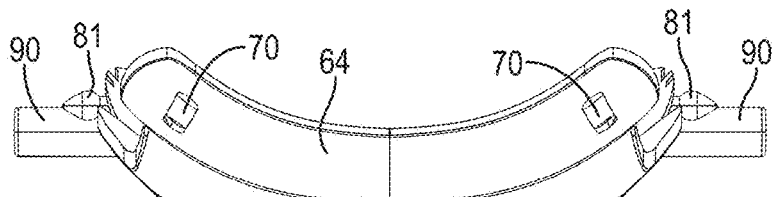
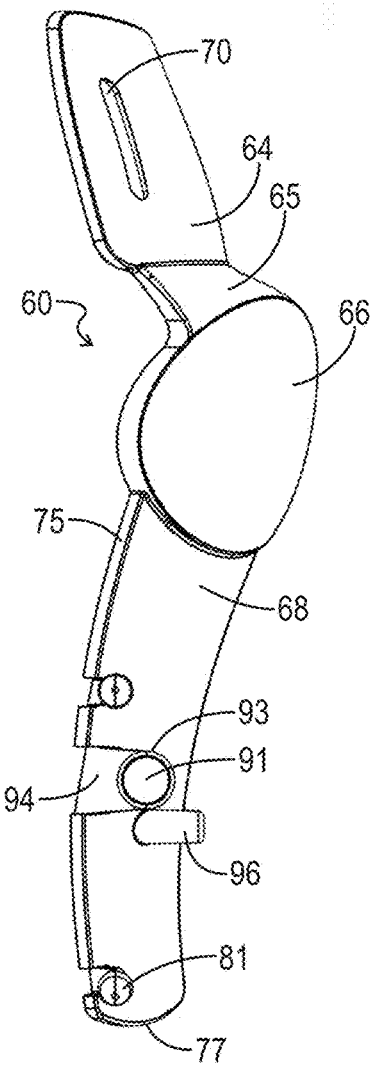
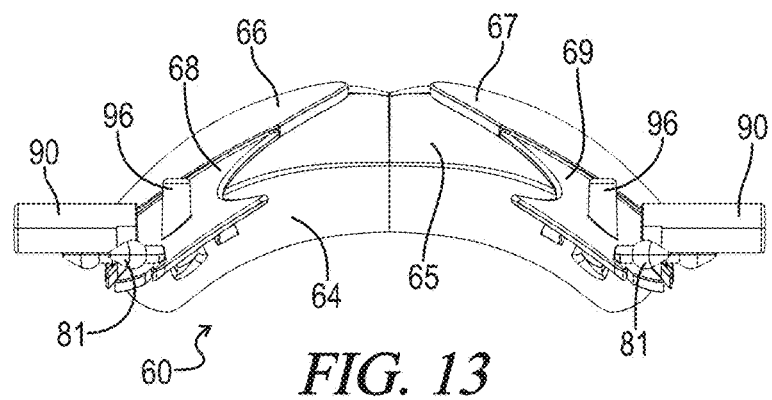
FIG. 11
FIG. 12
FIG. 13

DENTAL AEROSOL PROTECTION SYSTEM

FIELD OF THE INVENTION

The present invention relates generally to systems and devices for controlling dispersion of potentially hazardous aerosol and splatter particles produced during dental treatments and procedures. More particularly, the invention relates to a dental aerosol protection system which traps and collects aerosols and splatter droplets emitted from the oral cavity prior to being dispersed into the atmosphere, reducing the risk of transmission and exposure to airborne infectious diseases, including viruses such as COVID-19.

BACKGROUND OF THE INVENTION

Any discussion of the related art throughout the specification should in no way be considered as an admission that such related art is widely known or forms part of common general knowledge in the field.

Dental care professionals by necessity must work in close contact with their patients when performing dental procedures, and as a result are at risk of being exposed to aerosol and splatter particles expelled from the patient's oral cavity. Such particles may be expelled by the patient when talking, coughing, sneezing, or simply breathing, or may be generated by the procedure. Both splatter or droplet particles and bioaerosols may carry significant amounts of respiratory pathogens such as viruses, bacteria, and fungi. Viruses, particularly those causing respiratory and gastrointestinal infection, are the most common cause of infectious disease in indoor environments. Viruses responsible for respiratory infections include influenza viruses, rhinoviruses, corona viruses, respiratory syncytial viruses (RSVs), and parainfluenza viruses (PIVs), while viruses responsible for gastrointestinal infections include rotavirus, astrovirus, and Norwalk-like viruses (NLVs). Some infections, like the common cold, are very widely spread but are not severe, while others such as influenza-like infections are relatively more severe. A cough or sneeze possibly containing aerosolized influenza or coronavirus is especially concerning. Although dental professionals commonly utilize personal protective equipment such as masks, face shields, gloves, and gowns while treating patients, due to their small size dental aerosols may remain airborne long after the procedure has been completed and such protective equipment has been removed, increasing the likelihood of contamination.

In recent months, with the outbreak of the SARS-CoV-2 virus, oral transmission of dental aerosols and splatter has become an increasing concern, as many dental procedures use high speed handpieces or ultrasonic equipment, which instruments generate high levels of aerosols and splatter which are potentially harmful to the dentist or hygienist, dental staff, and patients present in the dental office. Use of such equipment has been reduced or delayed until the pandemic subsides, leaving patients without the benefit of certain treatments and procedures.

Endodontists routinely utilize a latex or nitrile dental dam during procedures that expose the interior of a tooth or require bonding. The dam is typically provided as a flexible, elastic rectangular sheet. One or more teeth to be treated are passed through a small hole made in the sheet, and a specialized clamp is then secured to the tooth to hold the dam in place. The edges of the dam sheet are stretched over projections on an outwardly facing surface of a frame positioned around the patient's oral cavity, such that the elastic nature of the dam sheet causes it to be secured to the frame.

Dental dams are effective in isolating teeth to be treated from the remainder of the oral environment of the mouth. The dam also reduces the volume of aerosol and splatter particles expelled from the patient's mouth by acting as a barrier between the front and back of the mouth. However, standard dental dams do not remove aerosol particles produced by the patient. In addition, there are many dental procedures in which aerosol production is extremely high and use of a rubber dam is not feasible. Examples include hygiene procedures where ultrasonic scaling is used, drilling a cavity with water spray coolant, and implant bone drills where a water spray is used to keep the bone from overheating. These procedures produce massive amounts of airborne bacteria, viruses, and fungi. Aerosols are quickly spread into the operatory and even into the ventilation system of the building, which puts many people at risk of contracting illness.

Handheld suction devices such as saliva ejectors for collecting moisture and high-volume evacuators (HVE) which draw relatively large volumes of air are also commonly used by dentists, but nevertheless do not provide a physical barrier between the patient and dental professional. There therefore remains an urgent need for devices and systems for limiting the spread of aerosols in an operatory, providing increased protection for dental professionals and reducing the likelihood of infection for all present in the dental office. Recognizing this need, the present inventor has developed a dental aerosol protection system that effectively traps and collects aerosol and splatter particles before they can escape the mouth area and become airborne in the operatory, and provides a barrier between the patient and dental professional. This system utilizes a high-volume suction to collect the trapped aerosol and splatter particles and drastically eliminates aerosols at the source, before they are introduced into the environment, and is adaptable and equally effective for use in dental procedures requiring a rubber dam and procedures where a rubber dam cannot be used.

BRIEF SUMMARY OF THE INVENTION

The present invention satisfies the above-described and other related needs by providing a dental aerosol protection system and method for use during aerosol and splatter generating dental procedures which provides a protective barrier between the dental professional and oral cavity of the patient, trapping and collecting potentially harmful particles prior to being dispersed throughout the operatory. In the several embodiments, the invention includes a ring assembly formed of an autoclavable plastic. In one mode of operation, the ring assembly is mountable to a supporting and protective face mask worn by the patient, while in another mode of operation the ring assembly and support mask can be used individually to protect dental professionals from exposure to aerosols and splatter depending upon the requirements of the particular procedure.

The ring assembly includes a frame sized and dimensioned to extend around the oral cavity during a dental procedure, and a collar which extends superiorly away from the patient. A lip projects inwardly from the collar and forms a circumferential ring, the inner edge of which defines a center lumen or operating field which is positioned directly over the oral cavity. A pair suction ports are joined to the ring assembly, each having a suction nozzle connectable on an end to a high velocity vacuum source by a suitable hose. The opposite end of each suction nozzle is open along an inner surface of the ring assembly, and in an embodiment open on an inner surface of the collar at a position behind or underneath the inner lip. The outwardly extending collar and inwardly directed lip jointly form a first extension which traps aerosol and splatter particles emitted by the patient underneath the first extension, and a high-volume suction at the suction ports simultaneously creates a circumferential negative pressure in close proximity to the patient's mouth, providing a funneling of air flow away from operating room towards suction ports of the device.

In another aspect, the dental aerosol protection system includes one or more flexible aerosol and splatter barrier extensions, which in an embodiment are made of a plastic film such as polyethylene. In an embodiment, the one or more flexible extensions are detachably secured to the ring assembly extending around the center lumen by elastic bands which are secured over connectors on the collar. The flexible extensions may be of different sizes and are oriented with one end tightly secured to the collar portion of the ring assembly and an opposite end extending superiorly away from the patient. The flexible extensions may be selectively positioned over the centrally located operating field and serve as another barrier between the patient's oral cavity and the operatory to further limit the spread of aerosols. The flexible extensions thus comprise an important component of the dental aerosol protection system in addition to the integral barrier formed by the collar and lip on the ring assembly. The flexible extensions are easily adjusted and repositioned by a dental professional as needed during each dental procedure without being obtrusive or hindering the dental professional's view or access to the oral cavity, and effectively contain aerosols and direct them into the high velocity vacuum ports.

In another aspect, the ring assembly may be utilized as a standalone aerosol and splatter containment device, such as in dental procedures requiring use of a conventional dental dam and where the dam is adequately held in place by a clamp secured to a tooth. In an embodiment, the frame portion of the ring assembly contains periodic spines over which the edges of the dam sheet are stretched and supported. Alternatively, the ring assembly may be connected to the supporting protective face mask structure, which holds or supports the ring assembly in a stable and balanced position on the patient. The support mask is a patient interface which is separately securable to the patient. In an embodiment, the support mask is integrally formed of a unitary clear or translucent plastic material and includes forehead, brow, eye, and cheek covering regions. The nose, mouth and chin areas of a patient wearing the support mask are left substantially uncovered by the support mask, allowing the patient freedom to breathe through both the nose and mouth, as well as complete freedom of jaw movement. An adjustable band or strap attached to the forehead covering region of the support mask is used to secure the mask to the patient. The brow and eye covering regions protect the patient's eyes (orbital process) as well as the upper part of the bridge of the nose, and are spaced outwardly away from the patient's face, slightly beyond where the lens of a pair of glasses would normally be located. The cheek covering regions extend downwardly over the cheek bones (malar process) on either side of the nose to a position below the corner of the patient's mouth. Posts located on the cheek covering regions of the support mask are configured to connect to corresponding sleeves on the ring assembly, and when connected secure the ring assembly over the front surface of the mask structure in a position extending between the cheek covering sections.

When the ring assembly and support mask are connected and worn by a patient, the center lumen or opening of the ring assembly will be positioned superiorly over or in front of the patient's oral cavity. In use during aerosol generating dental procedures, activation of the vacuum source attached to the suction port nozzles on the ring assembly by suction tubing will deliver a high-velocity suction circumferentially around the entire field of operation, drawing potentially harmful aerosols and splatter into the nozzles and away from the operating field before being emitted into the operatory. The flexible extensions are secured to the connectors on the ring assembly in the same manner regardless of whether the ring assembly is used as a standalone device or is attached to the support mask. In some embodiments, similar connectors are provided on the cheek covering regions of the support mask, such that the flexible extensions may be secured directly to the support mask instead of the ring assembly, which is advantageous where the dental professional prefers a larger diameter work area bordered by the extensions. Alternatively, the flexible extensions may be secured to connectors on both the ring assembly and support mask, wherein in one arrangement the flexible extensions on the support mask may be draped over the outer edges of the support mask as a further barrier to prevent aerosol particles from leaking between the support mask and face of the patient.

For aerosol generating dental procedures in which a dental dam is not suitable, and the dental professional prefers a larger work or operating field, in another aspect, integral suction ports are also provided on the cheek covering regions of the support mask. The suction ports on the support mask also include a nozzle which is similarly connectable to a high velocity suction source. The tab-like connectors on the support mask also enable one or more flexible extensions to be secured to the support mask in a position secured around the outer edges of the cheek covering regions and extending superiorly away from the patient around the nose and mouth area of the patient, such that the support mask also can be used as a standalone aerosol and splatter containment device. The flexible extensions serve as a barrier between the dental professional and the patient which aids in containing aerosol and splatter particles within the confines of the mask and extensions, and in guiding them towards the suction nozzle openings on the support mask. The flexible extensions are also easily maneuvered and positioned by the dental professional to suit the requirements of each individual procedure. Additional flexible extension barriers may also be positioned around the outer periphery of the outer edge of the ring assembly and support mask.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The accompanying drawing figures, which are incorporated in and form a part of the specification, are illustrative of aspects of the present invention which will become more fully understood together with the following detailed description, and are not meant to limit the scope of the disclosure in any manner, which scope shall be based on the claims.

FIG. 11 is a left-side elevation view of the support mask, the right-side elevation view being a mirror image thereof.

FIG. 12 is a top view of the support mask.

FIG. 13 is a bottom view of the support mask.

DETAILED DESCRIPTION OF THE INVENTION

Figure 1:
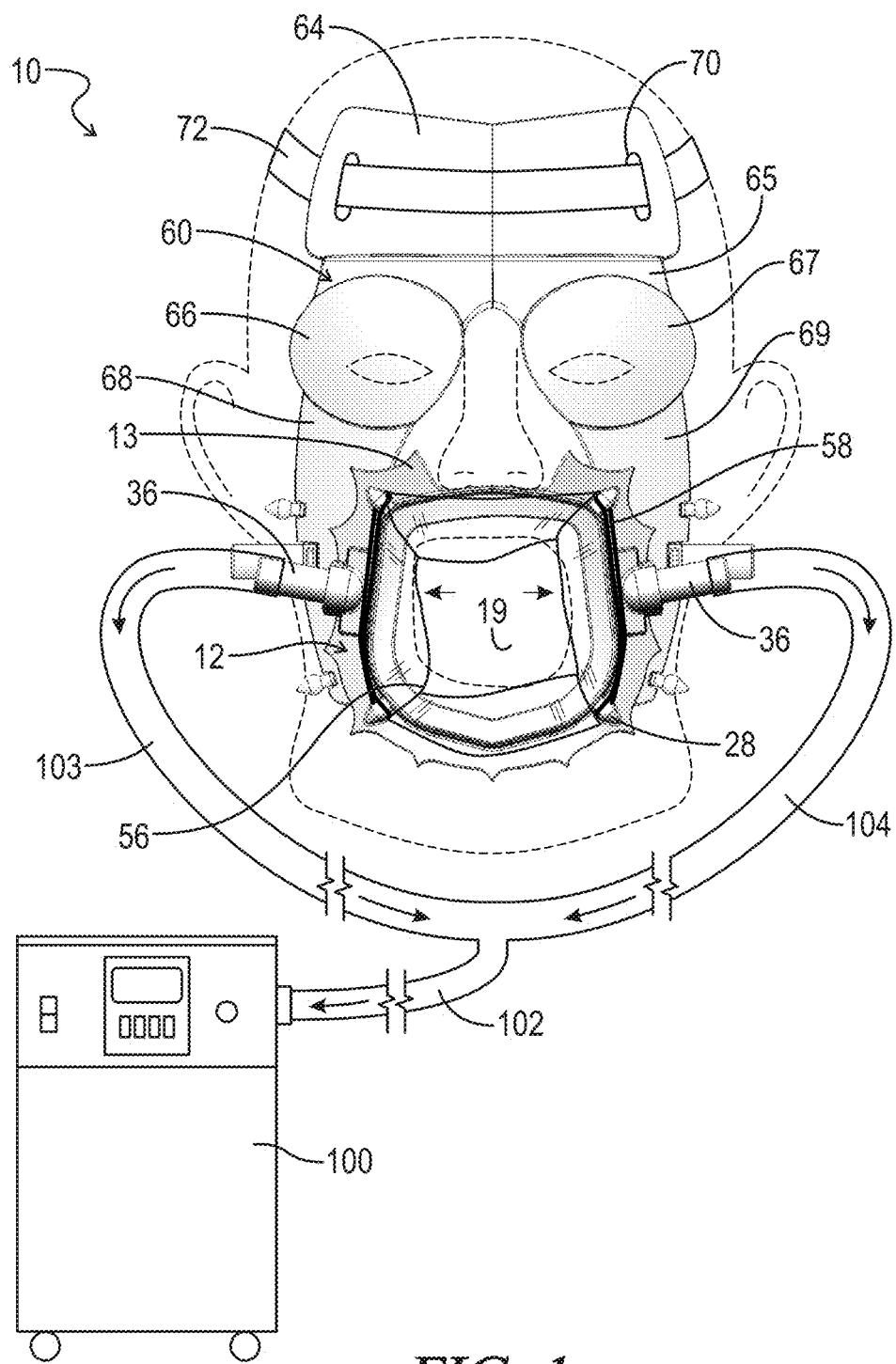
FIG. 1 is a diagrammatic view of an embodiment of a dental aerosol protection system in accordance with the present invention.

Reference will now be made in detail to embodiments of the present invention, examples of which are illustrated in the accompanying drawings. While the present invention will be described in conjunction with the various embodiment(s), such description is not intended to be understood in a limiting sense, but to be an example of the invention presented solely for illustration thereof, and by reference to which in connection with the following description and the accompanying drawings one skilled in the art may be advised of the advantages and benefits of the invention. On the contrary, the present invention is intended to cover alternatives, modifications, and equivalents, which may be included within the spirit and scope of the invention as defined by the appended claims. Further, it will be appreciated that embodiments of the present disclosure may employ any combination of features described herein. Descriptions of well-known starting materials, equipment, components and processing techniques may be omitted so as to not unnecessarily obscure the embodiments herein.

It is to be understood that the terminology used herein is for the purpose of describing particular embodiments only and is not intended to limit the full scope of the invention. The singular terms "a", "an" and "the", as used herein, are intended to include the plural forms as well, unless the context clearly indicates otherwise. The term "plurality", as used herein, is defined as two or more than two. The term "another", as used herein, is defined as at least a second or more. The terms "includes", "including" and/or "having", as used herein, are defined as comprising. The terms "joined" and/or "coupled," as used herein, are defined as connected, although not necessarily directly, and not necessarily mechanically. To aid in describing the disclosure, directional terms may be used in the specification and claims to describe portions of the present disclosure (e.g., front, rear, left, right, top, bottom, upper, lower, inner, outer, side, etc.). These directional are intended to merely assist in describing and claiming the disclosure, but the present disclosure is not limited thereto. The terms "comprises," "comprising," or any other variation thereof are intended to cover a non-exclusive inclusion, such that an article, apparatus, process, or method that comprises a list of elements does not preclude the presence or addition of other elements not expressly listed or inherent to such article, apparatus, process, or method. An element proceeded by "comprises . . . a" does not, without more constraints, preclude the existence of additional identical elements in the article, apparatus, process or method that comprises the element. The terms "about" or "approximately" as used herein apply to all numeric values, whether or not explicitly indicated. These terms generally refer to a range of numbers that one of skill in the art would consider equivalent to the recited values (i.e., having the same function or result). Elements which are identical, similar, or functionally identical are provided in the figures with the same reference numerals and a repeated description of these elements is in some cases dispensed with in order to avoid redundancies.

Figure 14:
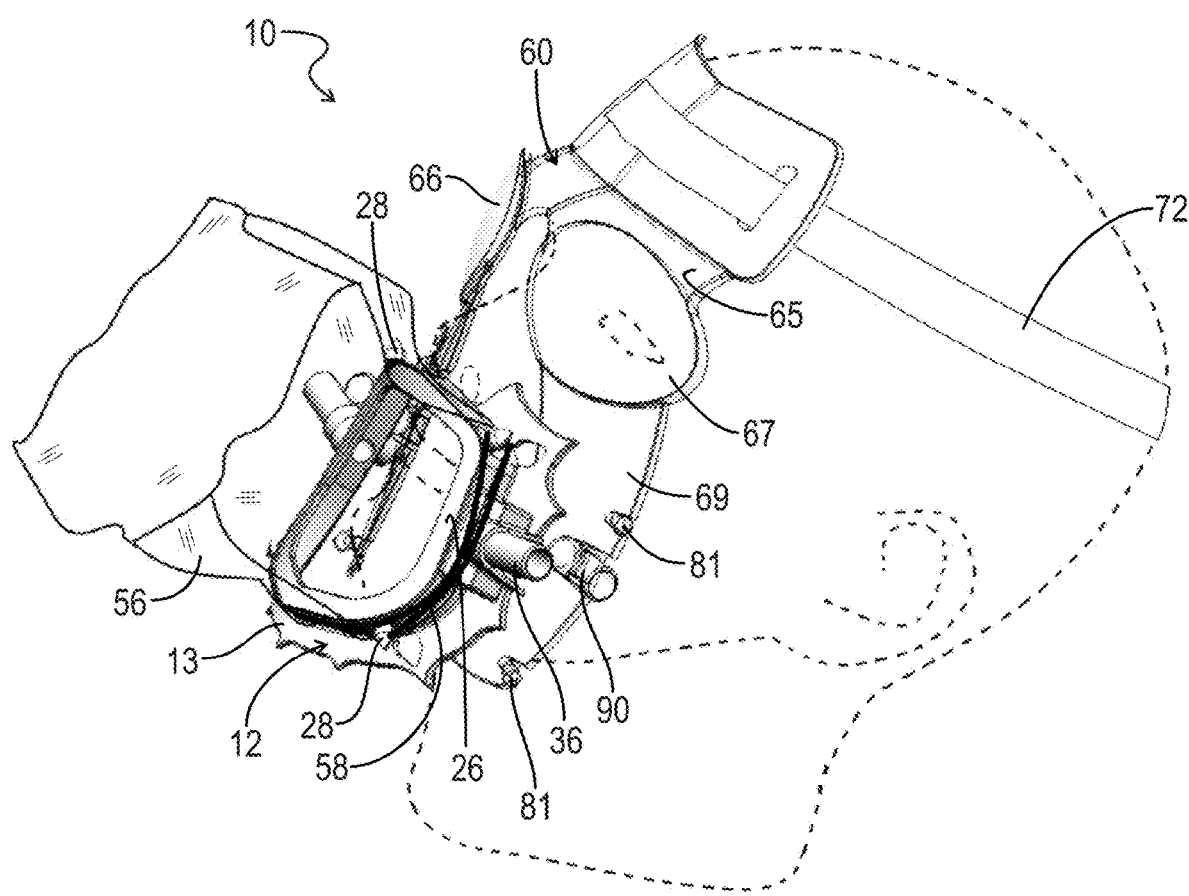
FIG. 14 is a right-side diagrammatic view of the connected ring assembly and support mask secured to a patient in a use position and having a flexible aerosol barrier extension attached to the ring assembly.
Figure 15:
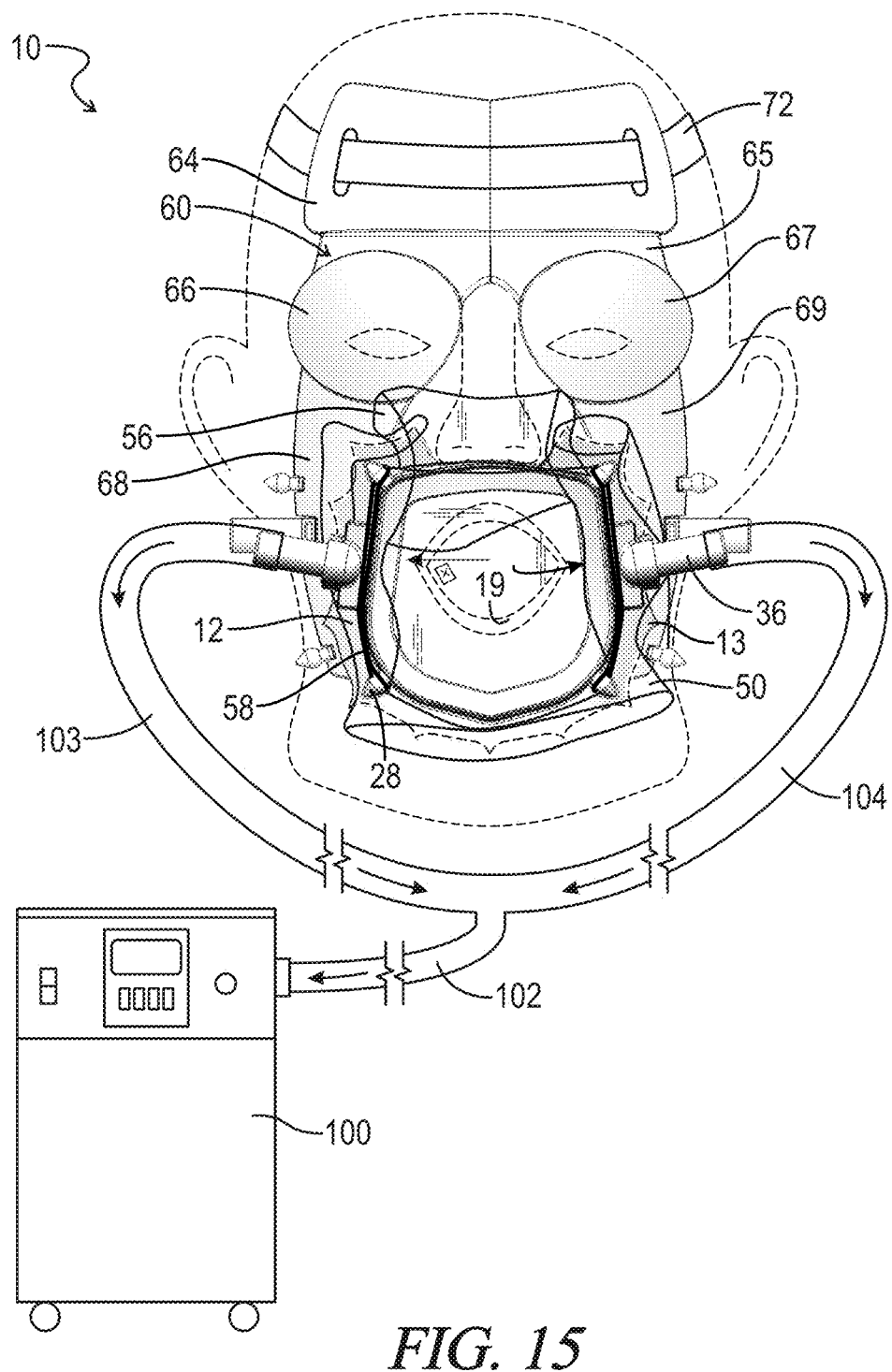
FIG. 15 is a diagrammatic view similar to FIG. 1 in which the ring assembly is also supporting a dam sheet.
Figure 16:
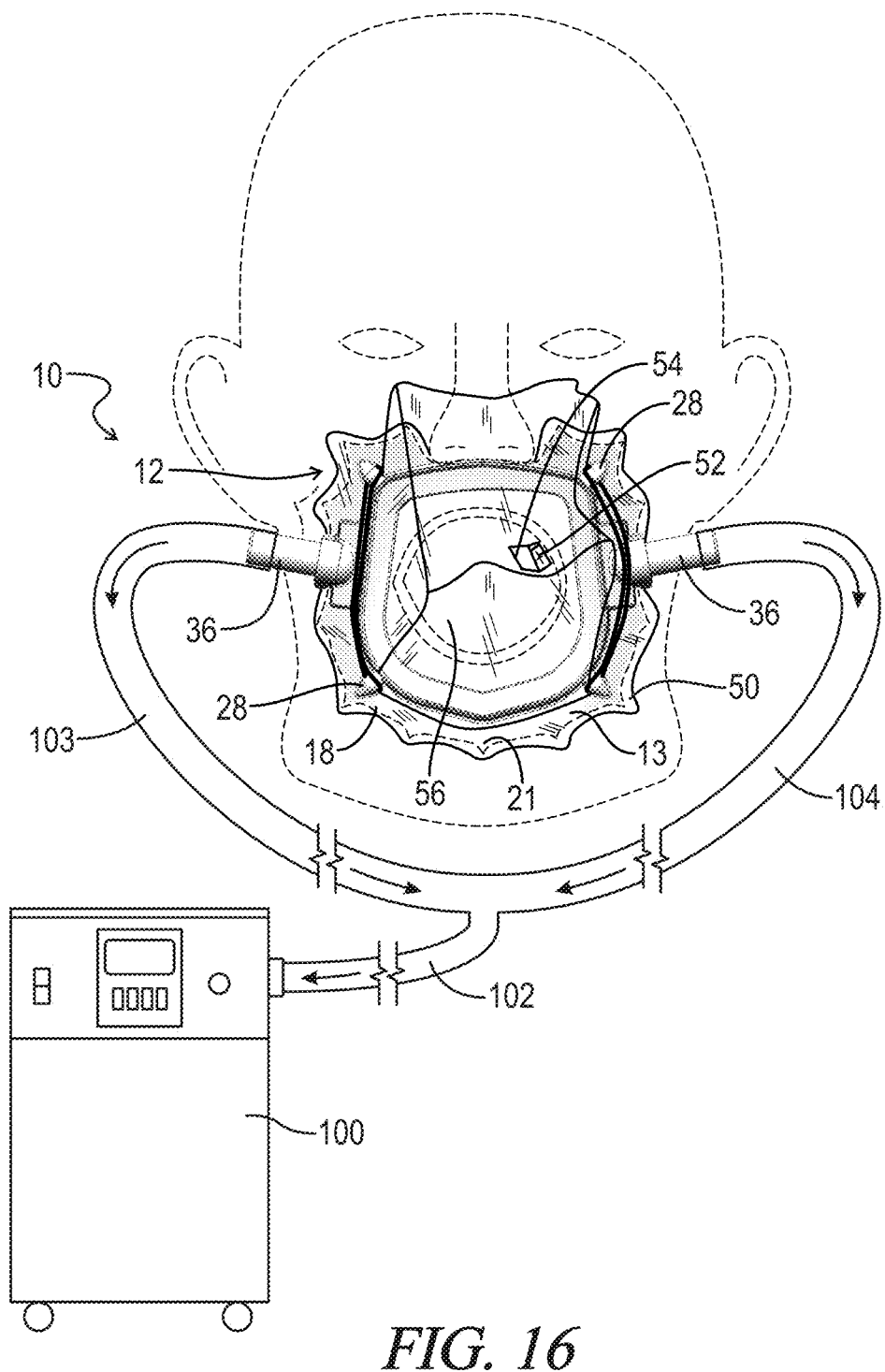
FIG. 16 is a diagrammatic view illustrating use of the ring assembly without the support mask including a dam sheet and a flexible aerosol barrier extension positioned around the field of operation.
Figure 17:
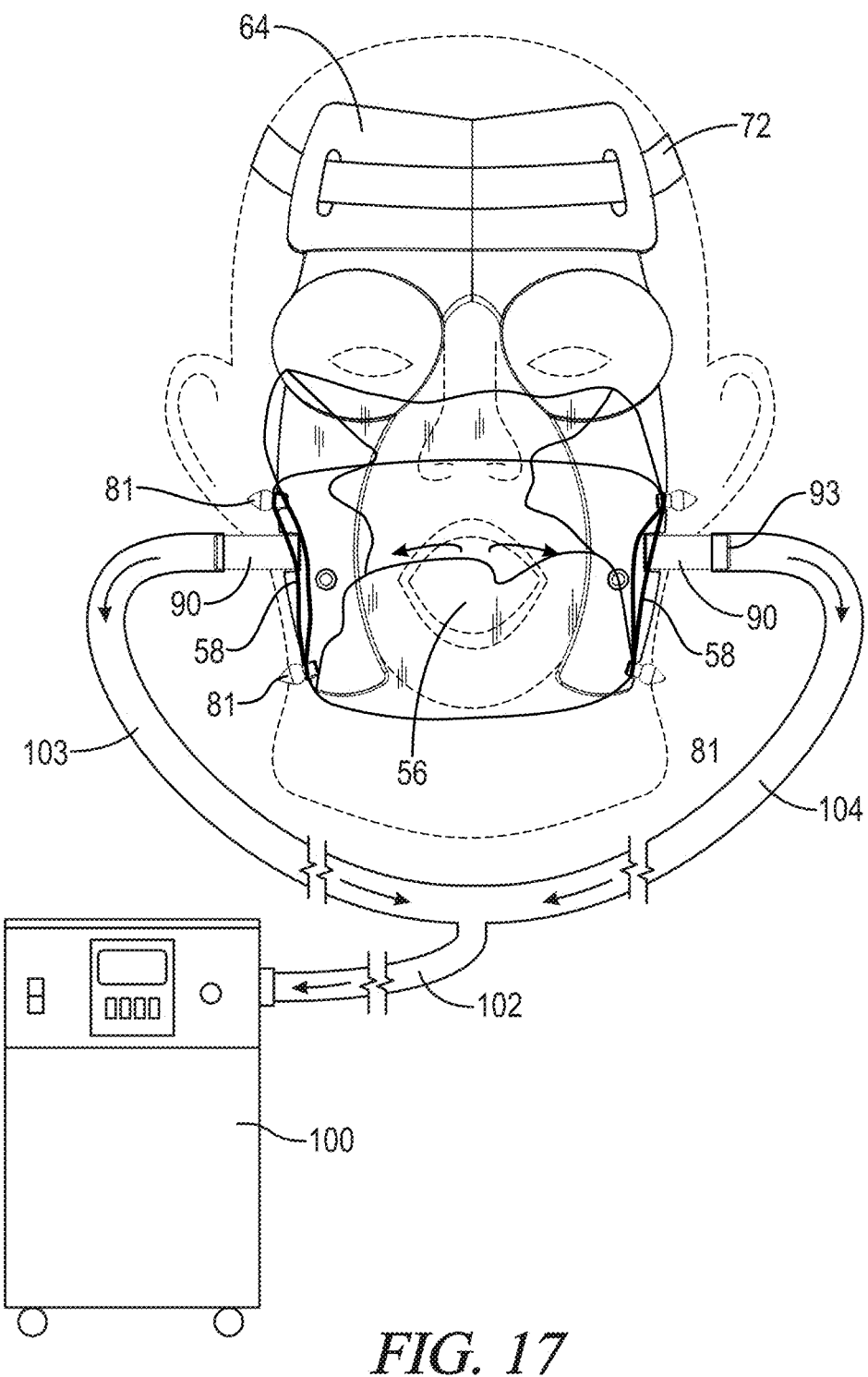
FIG. 17 is a diagrammatic view illustrating use of the support mask without the ring assembly and including a flexible aerosol barrier extension positioned around the field of operation.

The present invention provides a dental aerosol protection system particularly well adapted for controlling dispersion of and collecting aerosol and splatter particles emitted from the oral cavity of patients during dental procedures. FIG. 1 illustrates an embodiment of the system 10, which generally includes a ring assembly 12, a head-mountable support mask 60, and a high-speed dental vacuum source 100 which is shown connected to suction nozzles 36 on the ring assembly 12 by suction hoses 102, 103, and 104. As shown at least in FIGS. 2 and 3, the ring assembly 12 is detachably couplable to the support mask 60 such that depending upon the requirements of the particular dental procedure, the ring assembly 12 and support mask 60 may be utilized when coupled together as shown in FIGS. 1 and 14, or as shown in FIGS. 16 and 17 the ring assembly 12 and support mask 60 may be used separately to control dispersion of aerosols and splatter from a patient's mouth depending upon the requirements of the dental procedure. FIGS. 4-8 illustrate additional features of the ring assembly 12, FIGS. 9-13 illustrate additional features of the support mask 60, and FIGS. 14-23 illustrate various uses and alternative embodiments of the invention.

Figure 5:
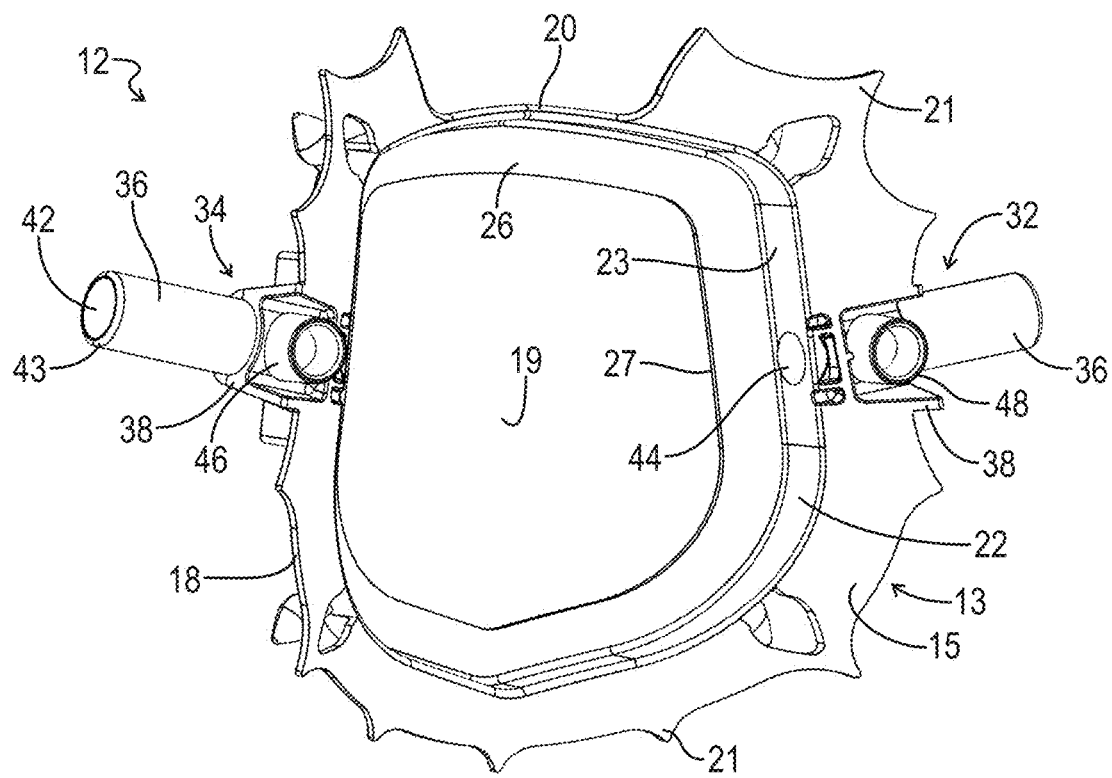
FIG. 5 is a rear isometric view of the ring assembly in FIG. 4.
Figure 6:
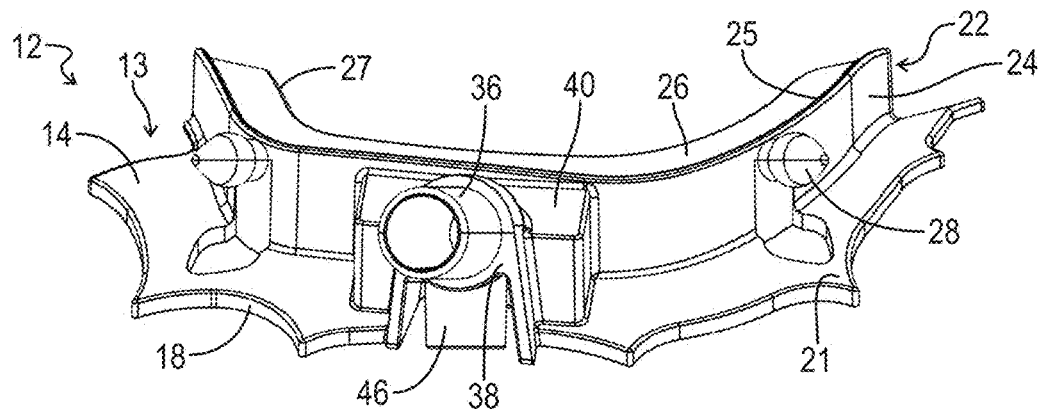
FIG. 6 is a left-side elevation view of the ring assembly, the right-side elevation view being a mirror image thereof.
Figure 7:
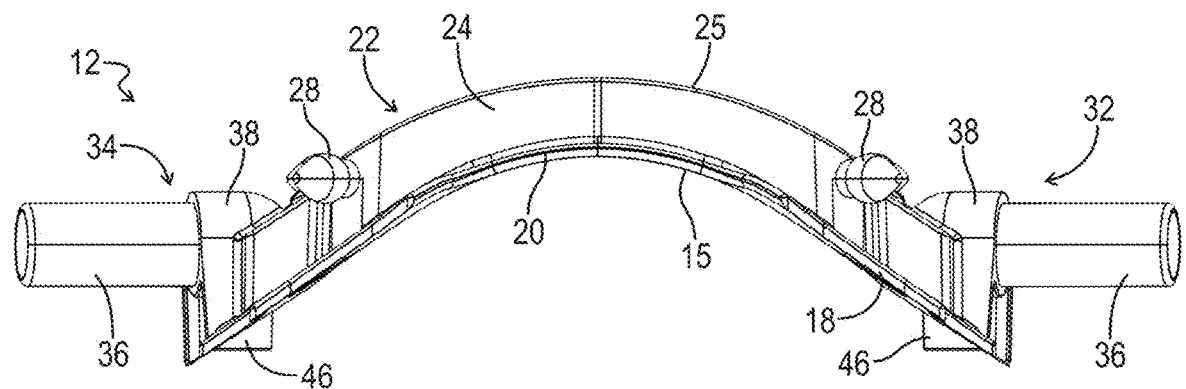
FIG. 7 is a top elevation view of the ring assembly.
Figure 8:
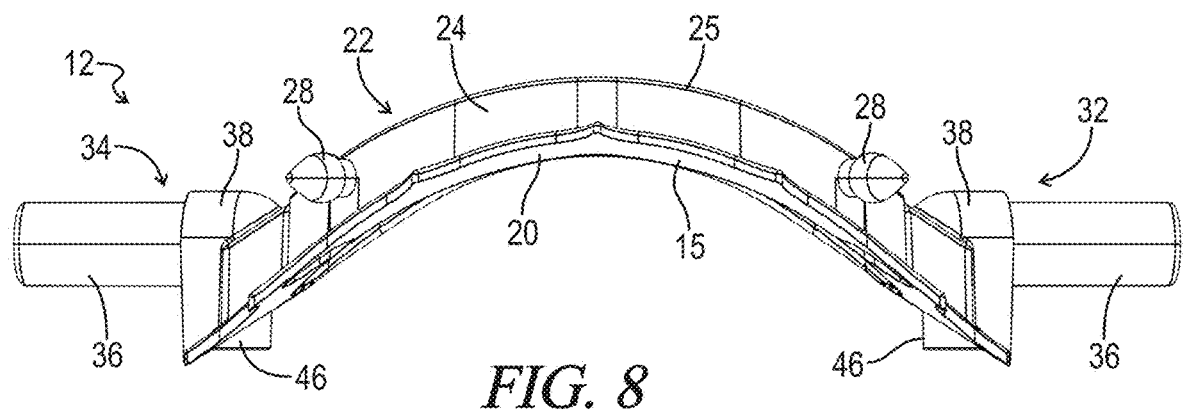
FIG. 8 is a bottom elevation view of the ring assembly.
Figure 9:
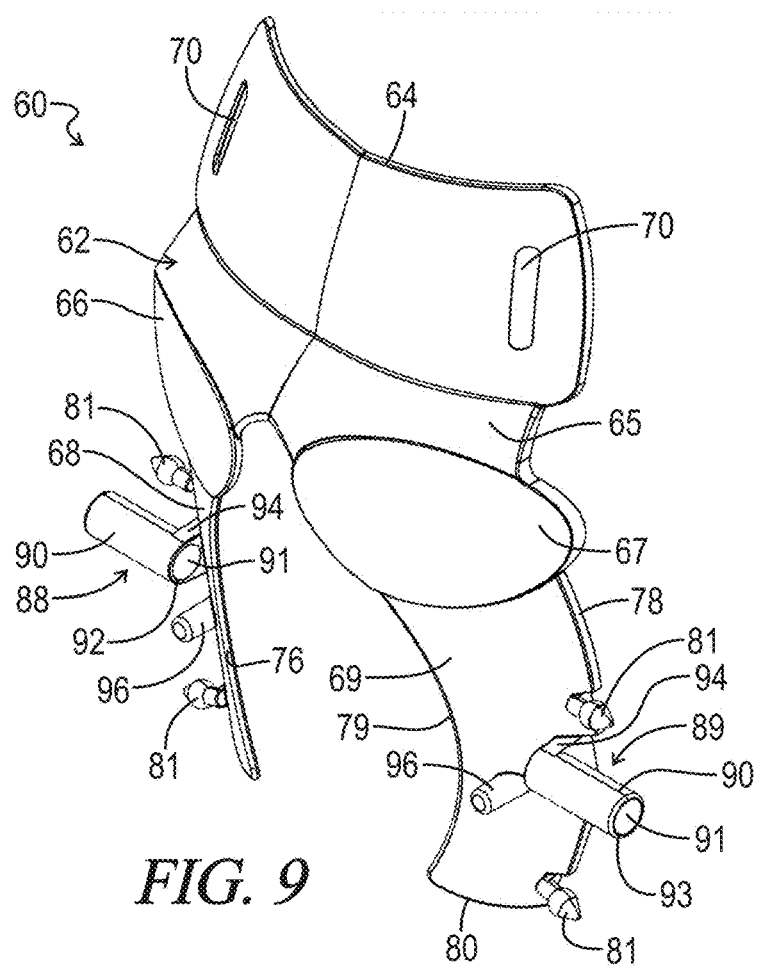
FIG. 9 is a front top isometric view of an embodiment of the support mask.
Figure 10:
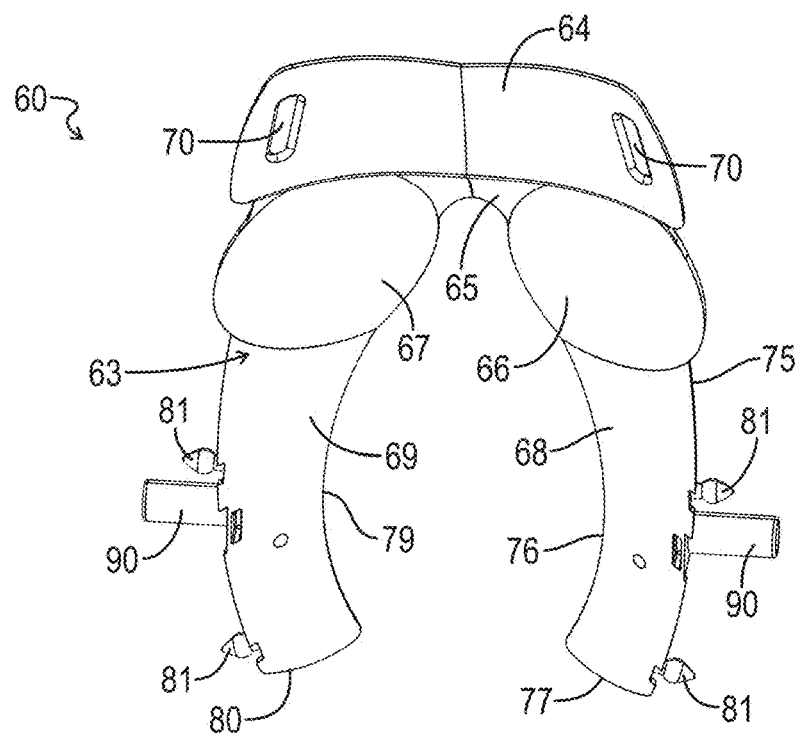
FIG. 10 is an isometric rear view of the support mask shown in FIG. 10.

Referring now to FIGS. 4-8, ring assembly 12 includes a thin frame 13 and has a front surface 14 and a rear surface 15. Frame 13 includes left, right and lower sides which generally form a U-shape, having an inner edge 16, and an outer edge 18. When in a use position on a patient, rear surface 15 is oriented towards the patient's face and front surface 14 is oriented away from the patient's face. As best illustrated in FIGS. 6-8, frame 13 has a curvature such that rear surface 15 is concave to follow the convex contours of the face and to facilitate a close fit with the face. Frame 13 is dimensioned to extend around the oral cavity of a patient undergoing a dental procedure, such that as shown in FIG. 1 a central opening or lumen 19 is positioned directly in front and over of the patient's open mouth. In the presently illustrated embodiment, frame 13 also has a cutaway or reduced width portion 20 along the upper side of ring assembly 12 such that the ring assembly 12 fits more comfortably over the upper lip area of a patient without interfering with the patient's nose or breathing.

Ring assembly 12 is preferably made of an autoclavable plastic and is manufactured using an injection molding and/or 3D printing process, although other suitable materials and conventional molding or cutting manufacturing techniques may alternatively be used. Assembly 12 may also be manufactured in different sizes for use with different age groups. When used without the support mask 60, portions of rear surface 15 along the outer periphery of frame 13 will be supported either directly or indirectly on the patient's face (see FIG. 16). In some embodiments, the outer edge 18 of frame 13 has a sinuating or dentate shape, forming a plurality of spaced apart outwardly directed spines or tines 21. As illustrated in FIG. 16, the spines or tines 21 are provided such that ring assembly 12 may be used to support a flexible, substantially planar dental dam sheet 50 of a type commonly used in certain dental procedures to isolate an area of the mouth from the remainder of the oral cavity. The largest commercially available rubber dam (dental dam) sheets typically are 6 inches by 6 inches, and therefore the frame portion will be large enough to support dam sheets of this size. The dam sheet 50 will first be secured in the patient's mouth around one or more teeth by a suitable clamp device, after which the outer edges of the dam sheet 50 are stretched over the rear side 15 of the frame 13 and then draped over the tines 21 and released, such that the stretchable dam sheet 50 is secured to frame 13.

Ring assembly 12 also includes a collar 22 which is joined to the inner edge 16 of frame 13 on an end. Collar 22 is oriented extending outwardly away from front surface 14, preferably along the entire inner edge 16 of frame 13, and has opposite inwardly and outwardly facing side surfaces 23 and 24, respectively and an outer edge 25. In addition, an inwardly directed lip 26 having a rim 27 is joined to collar 22 at a spaced location from inner edge 16 of frame 13, preferably in close proximity to outer edge 25. The inner rim 27 of lip 26 extends further inwardly on the ring assembly 12 than the inner edge 16 of frame 13, and thus defines the perimeter of the central lumen or opening 19 as well as the work or operating field 19 in which a dental professional has access to the oral cavity when using the device 12. In an embodiment, the dimensions of central lumen 19 as defined by inner rim 27 are about 2.5 inches from nose to chin and about 2 inches from left to right, although it will be understood that lumen 19 may have different dimensions in other embodiments. In the present embodiment, lip 26 is raised superiorly over the patient's mouth on collar 22, such that together collar 22 and lip 26 form a peripheral barrier or first extension which will trap significant amounts of aerosol and splatter particles expelled from the patient underneath the lip 26, which aerosols as explained in greater detail below will prevented from entering the operatory, instead being directed into high volume suction openings 44 formed in collar 22 underneath the lip 26.

Also joined to the ring assembly 12 on the outer surface 24 of collar 22 are several spaced-apart tab-like extension connectors 28, which as discussed in greater detail below are used to secure one or more additional flexible extensions or aerosol barriers to the ring assembly 12. Ring assembly 12 also includes one or more suction ports 32 and 34, which may be placed in fluid communication with high-velocity suction source 100 such as by suitable flexible suction lines or hoses 102, 103, and 104. Suction ports 32 and 34 are preferably integrally formed on ring assembly 12 at spaced apart locations on opposite sides of the work area 19. In the presently illustrated embodiment, suction ports 32 and 34 are located on the front surface 14 of frame 13 against the outer wall surface 24 of collar 22. Each suction port 32 and 34 includes a nozzle 36 which is joined to frame 13 and further supported by a strengthening or reinforcing structure 38. Reinforcing structure 38 is also joined to additional support housing 40 which connects to frame 13 and outer wall surface 24 of collar 22. Each nozzle 36 has an interior channel 42, and is oriented with outer end 43 extending outwardly away from frame 13. As shown in FIG. 5, the interior channel 42 of nozzle 36 has an inner end 44 which extends through collar 22 and forms a suction opening on the inner wall surface 23 of collar 22, underneath or behind the lip 26. In an embodiment, the diameter of interior channel 42 may narrow gradually from outer end 43 towards inner end 44 in order to increase the suction force generated at inner end 44.

Figure 24A:
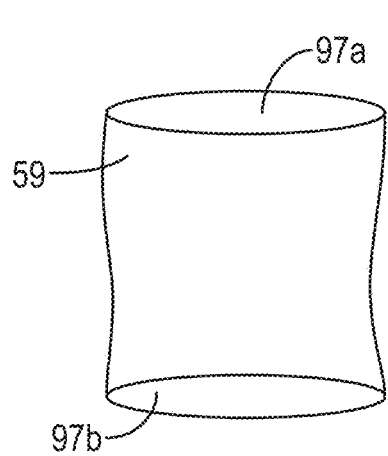
FIG. 24a illustrates one of the flexible extensions of the present invention.
Figure 24B:
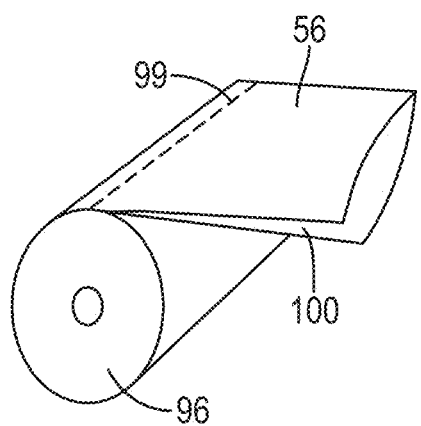
FIG. 24b illustrates an embodiment of the flexible extensions provided in a roll form.

Extension connectors 28 on collar 22 have a rounded shape (e.g. a bulb shape) and include a trunk section which is joined to collar 22, and an outer section at least a portion of which has a larger outer diameter than the trunk section. In the presently illustrated embodiment, connectors 28 extend away from the outer wall surface 24 of collar 22. As shown in FIGS. 1, 14, and 15, extension connectors 28 are used to secure one or more flexible aerosol side wall or barrier extensions 56 to the ring assembly 12. The flexible extensions 56 in an embodiment are made of a thin, clear plastic or plastic film with little rigidity, such as low-density or high-density polyethylene (LDPE, HDPE), while in other embodiments the extensions may be made of other suitable materials including but not limited to LLDPE or polyvinyl chloride (PVC), paper, and combinations of materials. The extensions 56 can vary in their dimensions and may be cut to different lengths according to the preference of the dental professional or the particular requirements of a dental procedure. Each extension 56 is preferably of a unitary construction generally having a tubular configuration with open opposite ends, although the extensions 56 may also be formed as a rectangular panel having its longitudinal or side edges sealed together or overlapping to form a unitary configuration. FIG. 24a illustrates one of the extensions 56 having a tubular form with open opposite ends 97a and 97b. FIG. 24b illustrates the extensions 56 provided in a roll form 98 with perforations 99 defining the individual extensions, which extensions 56 have open ends as well as an open longitudinal edge 100 such that the open edge can be easily overlapped, cut or otherwise fitted to the ring assembly 12 or face mask 60. The extensions 56 have a circumference sufficient for an open end of the extensions 56 to extend around and loosely fit over connectors 28 on the outer wall 24 of the collar 22, and in use form a flexible side wall around the work area 19 which can also be draped over the work area, and as explained herein further define an interior area in which a negative pressure is generated by the suction generating device 100 during use of the present invention.

As shown in FIGS. 1, 14, and 15, flexible extensions 56 are fastened to the extension connectors 28 by one or more securing members such as elastic bands 58. Each band 58 is positioned around at least one of the extension connectors 28 or pair of connectors as well as over an inwardly positioned end of the flexible extension 56. In other embodiments, the securing member may be a cap or clamp which fits over the connector 28 or other suitable securing apparatus. Once the extension 56 is secured to the connectors 28, the opposite outwardly directed end of the extension 56 is extended superiorly away from the patient such that the extension 56 forms a flexible barrier around the operating field 19. The extension 56 will then be positioned such that the outer end will drape inferiorly or towards the patient over the working area 19. While the extensions 56 have little rigidity, the material used in forming the extensions 56 should have a thickness and/or stiffness such that when extended superiorly the extension 56 will not collapse inwardly to a substantial degree under its own weight or due to the suction force generated when the high velocity suction source 100 connected to suction ports 32 and 34 is activated, but should also be sufficiently flexible to be easily moved or adjusted with only a slight manual pressure exerted by the dental professional. The extensions 56 in an embodiment are transparent such that the amount of light directed into the oral cavity by a light source in the operating room is not substantially reduced by the extensions, although in some embodiments an additional light apparatus may be connected to or otherwise utilized with the system 10. In an embodiment, the extensions 56 may be a LDPE poly tubing having a 2 mil thickness. The position and orientation of the flexible extensions 56 with respect to the work area 19 can be quickly and almost effortlessly adjusted as needed to alternatively cover and expose portions of the work area 19 as needed. When the dental procedure is completed, the flexible aerosol barrier extension 56 is removed from the connectors 28 by releasing the bands 58 and then safely discarded. It will be evident that the extensions 56 are not integrally formed as a part of the ring assembly 12, but rather are attachments which provide a barrier between the oral cavity of the patient and the dental professional, and also greatly enhance the capability of the system 10 to trap and collect aerosols which otherwise would be expelled into the operatory through central opening 19.

As shown in the rear view of ring assembly 12 in FIG. 5, a small section of frame 13 is cut away on the rear side of the reinforcing structures 38, and a pair of short tubular sleeves 46 extend rearwardly from reinforcing structures 38 in the area of the cutaway. As indicated above and shown in FIG. 1, the ring assembly 12 is designed to be coupled to support mask 60, which is a specifically designed patient interface capable of supporting the ring assembly 12 in an intended use position directly over the patient's oral cavity. The sleeves 46 serve as complementary fastener components which are used to matingly secure the ring assembly 12 to support mask 60, as described below.

Referring now to FIGS. 9-13, support mask 60 is preferably integrally formed as a unitary continuous piece of clear or translucent plastic such as a polycarbonate material, although in other embodiments the support mask 60 may be formed of two or more separate component parts which are joined during the manufacturing process, and may also be formed of other suitable materials or combinations of materials. Support mask 60 includes an anterior or front surface 62, a posterior or rear surface 63, a forehead covering region 64, a brow covering region 65, eye covering regions 66 and 67, and downwardly extending cheek covering regions 68 and 69. As shown in FIG. 17, the nose, mouth and chin areas of a patient wearing the support mask 60 are left substantially uncovered by the mask 60, allowing the patient freedom to breathe unencumbered through both the nose and mouth, and complete freedom of jaw movement.

Forehead covering region 64 comprises the uppermost portion of mask 60 and is dimensioned to extend over a major area of the forehead between the left and right temples. Region 64 has curvature such that posterior surface 63 is concave and contoured to the shape of an average forehead and fits closely to the forehead of the patient. Spaced apart slots or openings 70 are formed in the forehead covering region 64, preferably in relatively close proximity to opposing side edges of region 64. Slots 70 are configured to receive a band or strap 72 (see FIG. 1) which is passed through the slots 70. The band or strap 72 may be an elastic strap and is preferably length adjustable. It will be understood that the band or strap 72 may be connected to the mask 60 by other suitable means such as by an adhesive or other securing arrangement. Strap 72 is used to secure the support mask 60 to the patient's head with posterior surface 63 of forehead region 64 pressing against the patient's forehead. The large surface area of the forehead covering region 64 better supports and evenly distributes the weight of the mask 60. Forehead covering region 64 also preferably can bend or flex slightly in order to accommodate more or less pronounced forehead shapes. In embodiments of the present invention where the mask 60 is made of plastic, for patients allergic to plastic or otherwise where desirable, an intermediate layer such as a soft tissue paper can be placed between the patient's forehead and the posterior surface 63 of forehead region 64.

Brow covering region 65 is joined to the forehead covering region 64 along a lower edge of the forehead covering region 64, and eye covering regions 66 and 67 are similarly joined to brow covering region 65 along a lower edge of the brow covering region 65. The brow and eye covering regions 65 and 66-67, respectively, are fabricated to provide protection around the patient's eyes (orbital process) and upper part of the bridge of the nose. Brow covering region 65 in the illustrated embodiment extends substantially over the patient's entire brow area, while eye covering regions 66 and 67 substantially cover the patient's left and right eye areas. As best shown in FIG. 11, brow covering region 65 is angled forwardly and protrudes forwardly or outwardly with respect to forehead covering region 64. As a result, when support mask 60 is secured to the patient by strap 72, both the brow covering region 65 and eye covering regions 66 and 67 will be spaced apart or positioned superiorly away from the patient's face, preferably a distance slightly beyond where the lens of a pair of glasses would normally be located. The resulting space between the rear surface of the brow and eye covering regions 65 and 66-67 is more comfortable for the patient, allows for anatomical variance between different patients such that the support mask 60 fits a broader range of patients, and protects the eyes in a manner similar to a pair of safety glasses.

Cheek covering regions 68 and 69 of mask 60 are joined to eye covering regions 66 and 67 along the lower edge of eye covering regions 66 and 67, respectively, and are continuous with the eye covering regions 66 and 67. Cheek covering region 68 has an outer margin 75, an inner margin 76, and a lower margin 77, while cheek covering region 69 similarly has an outer margin 78, an inner margin 79, and a lower margin 80. Cheek covering regions 68 and 69 are substantially mirror images of each other, as are eye covering regions 66 and 67. The posterior surface 63 of cheek covering regions 68 and 69 is slightly concave. In addition, the outer margins 75 and 78 of cheek covering regions 68 and 69 have a slight outward or convex curvature extending from eye covering regions 66 and 67 to lower margins 77 and 80, respectively. The inner margins 76 and 79 of cheek covering regions 68 and 69 have a more pronounced inward or concave curvature extending from eye covering regions 66 and 67 to lower margins 77 and 80, respectively. When support mask 60 is worn, cheek covering regions 68 and 69 extend downwardly over of the cheek bones (malar process) on either side of the nose, and there is an open area between regions 68 and 69 for the lower nose and mouth which are left uncovered by the support mask 60. The outward curvatures of cheek covering regions 68 and 69 provide an even larger work field for the dental professional. The lower margins 77 and 80 of regions 68 and 69 should extend below the corner of the patient's mouth.

Figure 18:
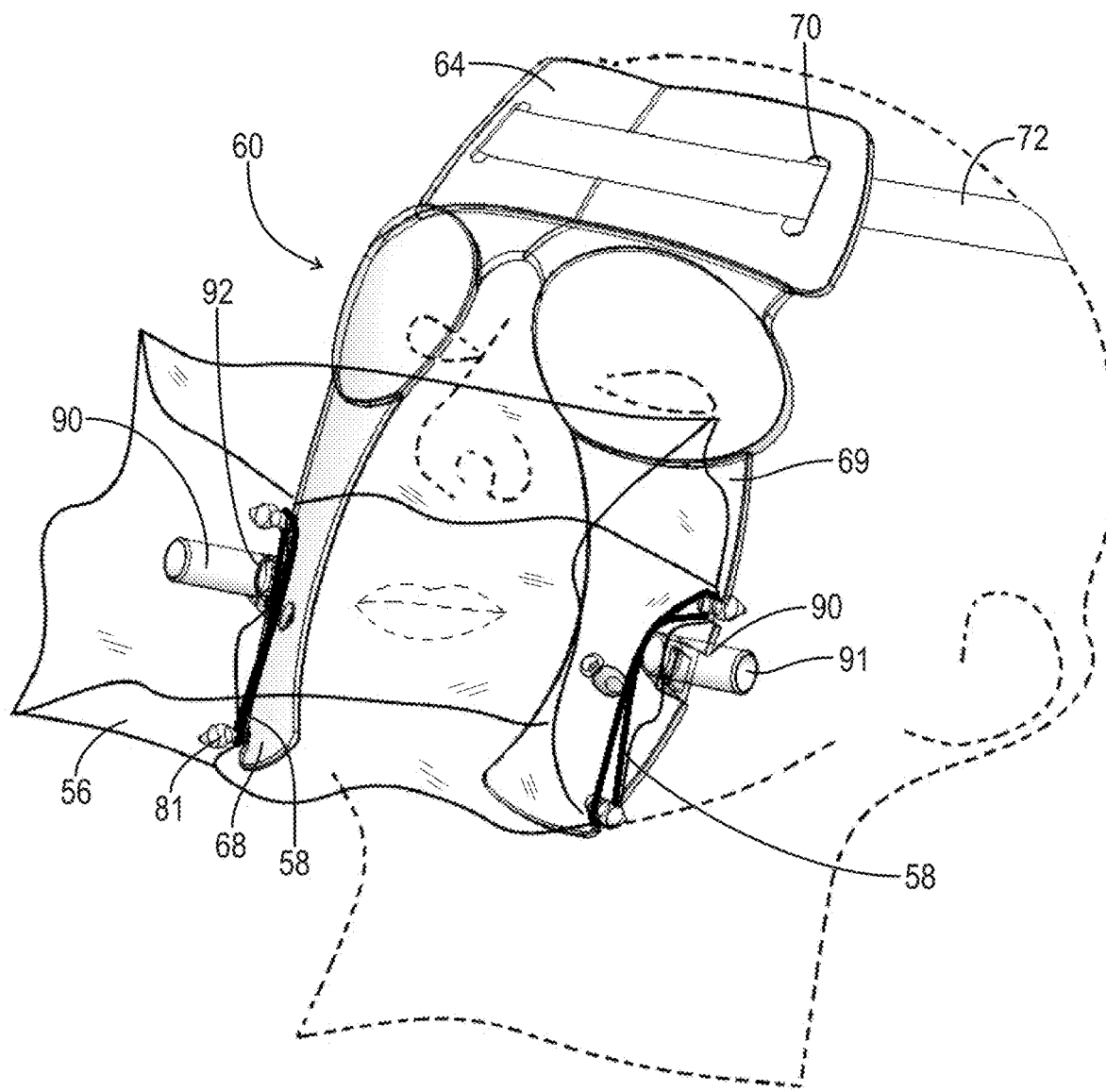
FIG. 18 is a front right-side view of the support mask including a flexible aerosol barrier extension as used without the ring assembly.

At least one pair of tab-like extension connectors 81 is joined to each of the cheek covering regions 68 and 69. Extension connectors 81 are similar in structure to extension connectors 28 provided on the ring assembly 12 discussed above, and include a cylindrical trunk section attached to cheek covering region 68 or 69, followed by a larger diameter outer section. The connectors 81 are spaced apart along outer margins 75 and 78 of the cheek covering regions 68 and 69, respectively, and are oriented such that they protrude away from the outer margins 75 and 78. As best shown in FIGS. 17 and 18, connectors 81 facilitate attachment of one or more flexible extensions 56 to the cheek covering regions 68 and 69 of the support mask 60 using one or more securing members such as elastic bands 58 which are secured over the connectors 81 after an extension 56 is positioned over the connectors 81, holding a lower portion of the extensions 56 to the connectors 81. It will be evident therefore that the flexible aerosol barrier extensions 56 may be similarly coupled to either the ring assembly 12 or the support mask 60, the advantages of which arrangement are discussed below.

The presently described embodiment of support mask 60 also includes a pair of suction ports 88 and 89 which are joined to mask structure 60 at an intermediate position along the outer margin 75 and 78 of the cheek covering sections 68 and 69, respectively. Each suction port 88 and 89 includes a suction nozzle 90 having an interior channel 91 which is open on opposite inner and outer ends 92 and 93, and a support frame 94 joins the nozzle 90 to the respective cheek covering region 68 and 69. Frame 94 of suction port 88 supports nozzle 90 in an orientation with inner end 92 extending over the anterior surface 62 of the cheek covering region 68, facing towards inner edge 76, and with outer end 93 oriented extending outwardly away from outer margin 75. Similarly, frame 94 of suction port 89 supports nozzle 90 with inner end 92 extending over the anterior surface 62 of the cheek covering region 69, facing towards the inner edge 79, and with outer end 93 oriented extending outwardly away from outer edge 78. Each nozzle 90 is positioned to be directly along the sides of the mouth and oral cavity of a patient wearing the support mask 60.

Figure 2:
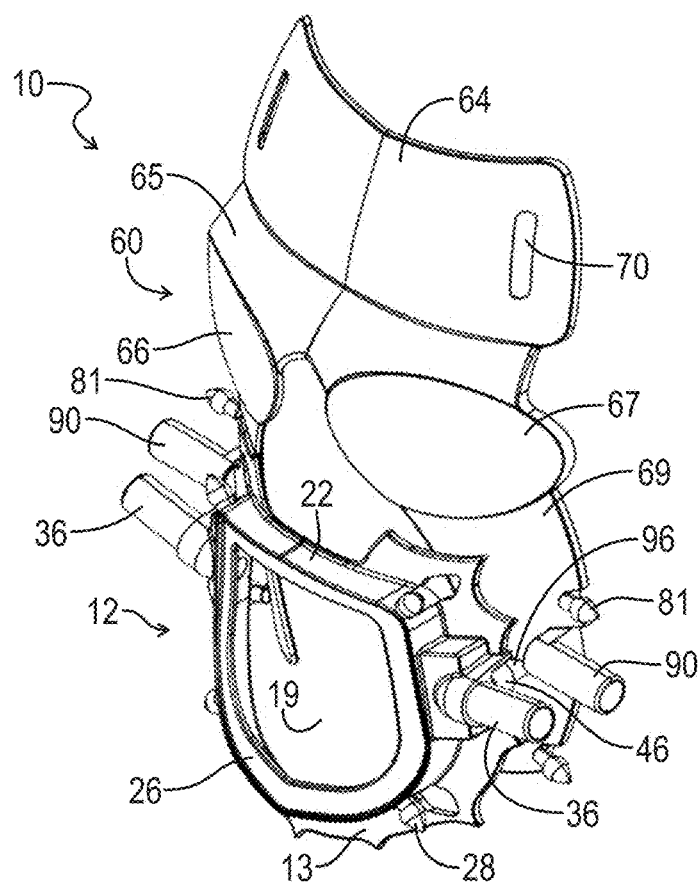
FIG. 2 is an isometric view of a connected ring assembly and mask structure in accordance with the invention.
Figure 3:
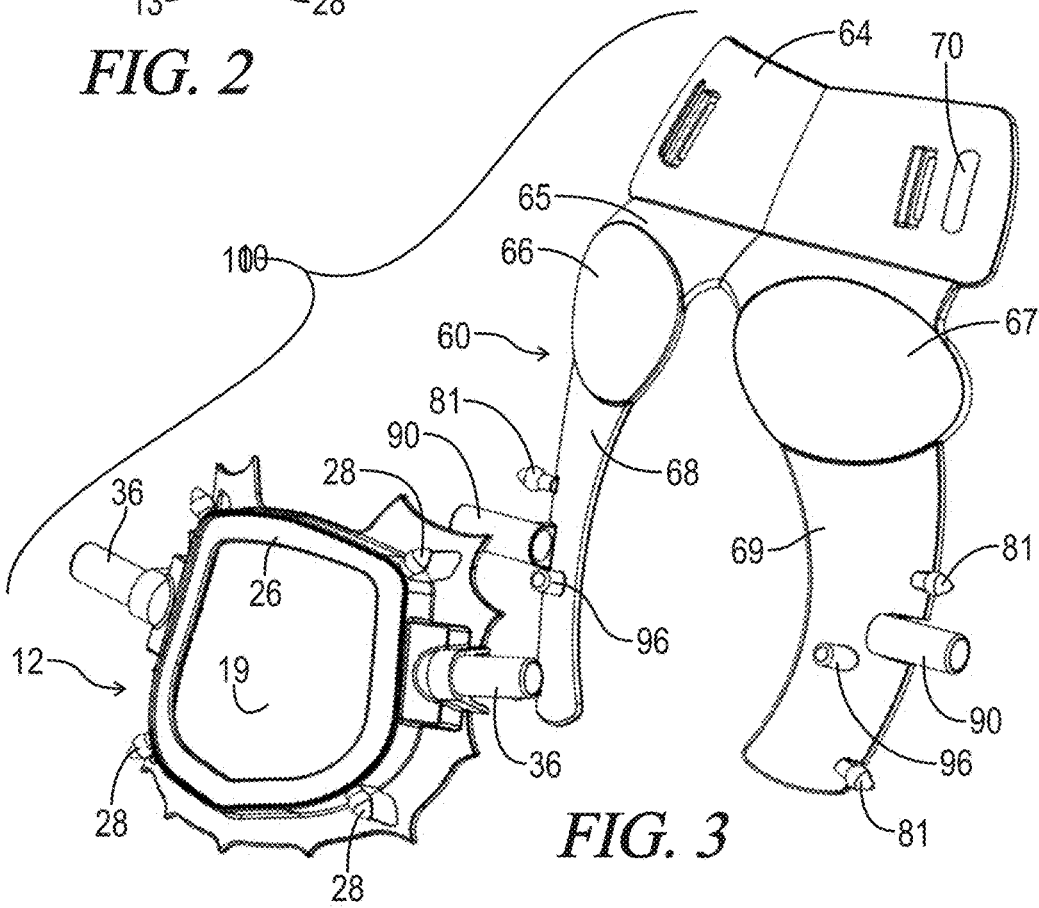
FIG. 3 is an exploded view of the ring assembly and mask structure shown in FIG. 2.
Figure 4:
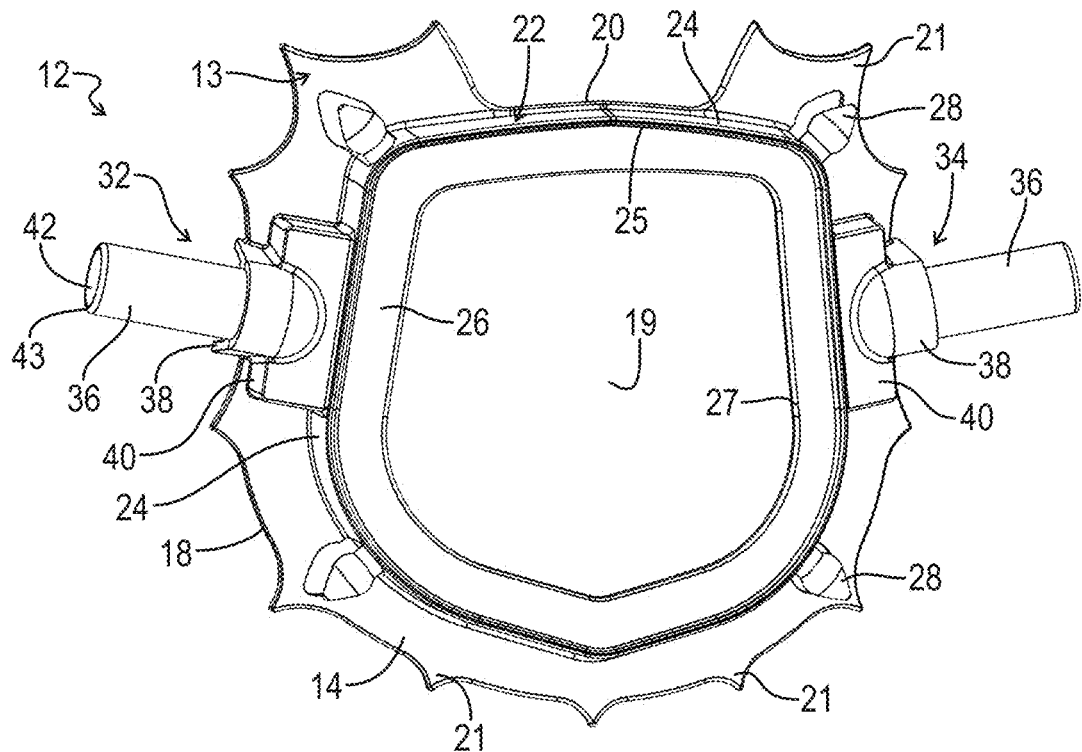
FIG. 4 is a front isometric view of an embodiment of the ring assembly.

Also attached to the cheek covering sections 68 and 69 of support mask 60 projecting outwardly from anterior surface 62 are mounting posts 96. As illustrated in FIGS. 2 and 3, each post 96 is sized and positioned to serve as a mating fastening component with connector sleeves 46 on the rear surface 15 of ring assembly 12. Mating fastening components 46 and 96 thus enable the ring assembly 12 and support mask 60 to be detachably joined. In an embodiment, the outer edge of the posts 96 has an outer circumference or shape substantially the same as the inner circumference or shape of the hollow connector sleeves 46, such that a friction fit between sleeves 46 and post 96 is provided when posts 96 are received in sleeves 46. As illustrated in FIG. 1, when the support mask 60 is secured to a patient by strap 72 attached to brow covering region 64 as described above, and ring assembly 12 is joined to the support mask 60 by sleeves 46 and matching prongs 96, the center lumen or opening 19 of the ring assembly 12 by necessity will be desirably positioned directly over the patient's open mouth. Posts 96 therefore provide direct support and positioning of the ring assembly 12 on the support mask 60. It will be understood that the ring assembly 12 can be attached to the support mask 60 by other securing or alignment arrangements including but not limited to a snap fitting or other compression-type fittings.

When the ring assembly 12 and support mask 60 are connected, in one mode of operation, shown in FIG. 1, the suction nozzles 36 of suction ports 32 and 34 on ring assembly 12 are coupled on their outer ends 43 to suction generating device 100 by suitable flexible connecting hoses or tubing. Device 100 will typically but not necessarily be a high-speed dental vacuum system of a type used and already installed in most dental offices. An example of a suitable system is the ADC V105 External Oral Suction device manufactured by Affordable Dental Chairs, Inc. A suction force suitable for most dental procedures and for use in the present invention is between 11 to 12 bars. The connecting hoses or tubing may be a high-performance suction tube that will be connected in fluid communication between the outer end 43 of nozzles 36 of suction ports 32 and 34 on ring assembly 12 and a suction port on the dental vacuum system 100. In FIG. 1, a long tail section of tubing 102 connects to the vacuum system 100 on one end and to a t-connector, not shown, on the other end. The t-connector then connects to a pair of shorter-length respirator tubes 103 and 104, while are also each connected to one of the nozzles 36 on suction ports 32 and 34. As indicated by the arrows in tubes 102-104, when the vacuum unit 100 is activated, a high powered vacuum suction is generated at the inner end 44 of suctions nozzles 36 on the inner surface 23 of collar 22, generating a negative pressure and vortex around the oral cavity that draws in aerosolized particles. In another mode of operation, the suction hoses or tubing attached to the suction generating device 100 may be connected both to nozzles 36 on the ring assembly 12 and to nozzles 90 on the support mask 60, providing an aerosol collecting suction force at four separate locations around the oral cavity rather than two. Alternatively, the suction hoses or tubing may be connected only to suction nozzles 90 on the support mask 60, which may be preferred by dental professionals who also prefer to attach the flexible extensions 56 to connectors 81 along the outer margins or edges 75 and 78 of cheek covering regions 68 and 69 of mask 60 rather than to connectors 28 on the ring assembly 12 in order to provide a larger work area bordered by the extensions 56. Additional plastic extensions 56 can also be positioned extending over the outer edges of the mask and cheek and jaw area of the patient in order to minimize leakage.

When the ring assembly 12 is attached to the support mask 60, as shown in FIGS. 1 and 14, the weight of the ring assembly 12 will be more evenly distributed on the patient. It is particularly beneficial to use the support mask 60 to hold the ring assembly 12 in a secure and stable position around the patient's mouth for certain procedures where a dental dam sheet 50 cannot be stably or tightly secured in position around a tooth by a clamp or the like. In addition, using the ring assembly 12 and support mask 60 together is beneficial in procedures where a rubber dam is not required. This includes numerous dental procedures but especially hygiene procedures and implant procedures where use of a rubber dam is not possible, but high levels of contaminated aerosols are generated, all of which procedures are made much safer from using the present system 10. The support mask 60 will rest securely on the patient's face with rear surface 63 of forehead covering region 64 in contact with the forehead area, and with a portion of the inner surface of the cheek covering regions 68 and 69 resting against the check bone or Malar process. If the ring assembly 12 is used without the mask 60 with a dental dam 50 that is not adequately secured to a tooth, a slight turn of the head or sneeze by the patient, or a slight contact of the dental professional's hand against the assembly 12 may cause it to become ajar. The mask 60 therefore provides the additional support required to maintain the ring assembly 12 in a stable position around the oral cavity of a patient.

FIG. 16 illustrates the ring assembly 12 in use with a dental dam sheet 50 without the support mask 60. A small hole is made in the dam sheet 50 through which a tooth 52 to be treated is passed, thereby isolating the tooth 52 from the rest of the oral cavity. A clamp 54 of a conventional type familiar to those skilled in dentistry is utilized to hold the rubber dam sheet 50 around the isolated tooth 52. The ring assembly 12 is then positioned over the front of the dam sheet 50 with rear surface 15 facing the patient, and the rubber dam sheet 50 is stretched outwardly and then folded or draped forwardly over tines or spines 21 on the outer edge 18 of the frame 13. Due to the flexible and elastic nature of the dam sheet 50, once draped over the spines 21 and released the sheet material will retract and be adequately secured to the frame 13. Since the patient will be in a reclined position, the combination of the dam sheet 50 being secured to the tooth 52 by clamp 54 and to the ring assembly 12 by spines 21 is sufficient under normal conditions to hold the ring assembly in a position with central opening 19 which defines the work area centered over the patient's open mouth. In still another use arrangement, the dental dam sheet 50 may be secured to conventional dam frame, and the device 12 may then be overlaid on the conventional dam frame and sheet when desired, which makes it possible to easily remove and replace the ring assembly 12 without first disengaging the dam sheet from the frame 13.

FIGS. 17 and 18 illustrate the support mask 60 in another mode of operation in use as a standalone aerosol protection device without ring assembly 12. In this mode of operation, extension connectors 81 on cheek covering regions 68 and 69 which are positioned around the field of operation are used to connect one or more flexible plastic aerosol barrier extensions 56 to the mask structure 60 by securing members such as elastic bands 58 which are positioned over the connectors 81 and inner end of the extensions 56. Once connected to the support mask 60 by connectors 81, the extension or extensions 56 are then arranged to extend superiorly away from the mask 60 and face of the patient, providing a flexible aerosol and splatter containment barrier extending around and outward from the work area, which barrier can be easily repositioned or adjusted by the dental professional as needed during a procedure. One or more additional extensions 56 may also be positioned between the outer margins 75 and 78 of cheek covering regions 68 and 69 and the patient's face to prevent any leakage in this area. It will be understood that other arrangements for securing the extensions 56 to the ring assembly 12 or support mask 60 may be utilized, such as an adhesive or differently shaped connector, while still falling within the intended scope of the invention. The outer end 93 of the nozzles 90 is in a convenient location to attach the suction tubing 103 and 104, which tubing in turn is connectable to a high-volume suction source 100 of a type already found in most dental offices. As shown in FIG. 17, the inner end 92 of the nozzles 90 is positioned over the front surface 62 of the cheek covering regions 68 and 69 and is facing in the direction of the inner edge 76, 79 of the cheek covering region 68, 69, respectively, ensuring that the suction force generated in channels 91 of nozzles 90 is directed towards the work area between cheek covering regions 68 and 69, and is optimally positioned to draw in aerosol and splatter particles emitted from the patient's mouth. In addition, the flexible extensions 56 provide an effective adjustable physical barrier between the oral cavity of the patient and the dental professional and operatory. Aerosolized particles expelled from the oral cavity which otherwise may have been escaped past the nozzles 90 will now be prevented from escaping into the operatory and will be drawn towards the nozzles 90. The flexible extension 56 in combination with suction nozzles 90 air will create a negative pressure within the work area and tend to cause air to flow towards the nozzles 90, indicated by the arrows in FIG. 17, rather than superiorly away from the patient. This air flow will both greatly reduce the number of aerosol particles which are able to escape beyond the extensions 56, and also will tend to draw aerosol particles back towards suction nozzles 90, without significantly hindering the ability of the dental professional to complete the dental procedure. The ability of the mask structure 60 as well as the ring assembly 12 to provide and maintain a constant hands-free high-volume suction force in close proximity to and on opposite sides of the operative site greatly expands the usefulness of the mask device 60.

Figure 19:
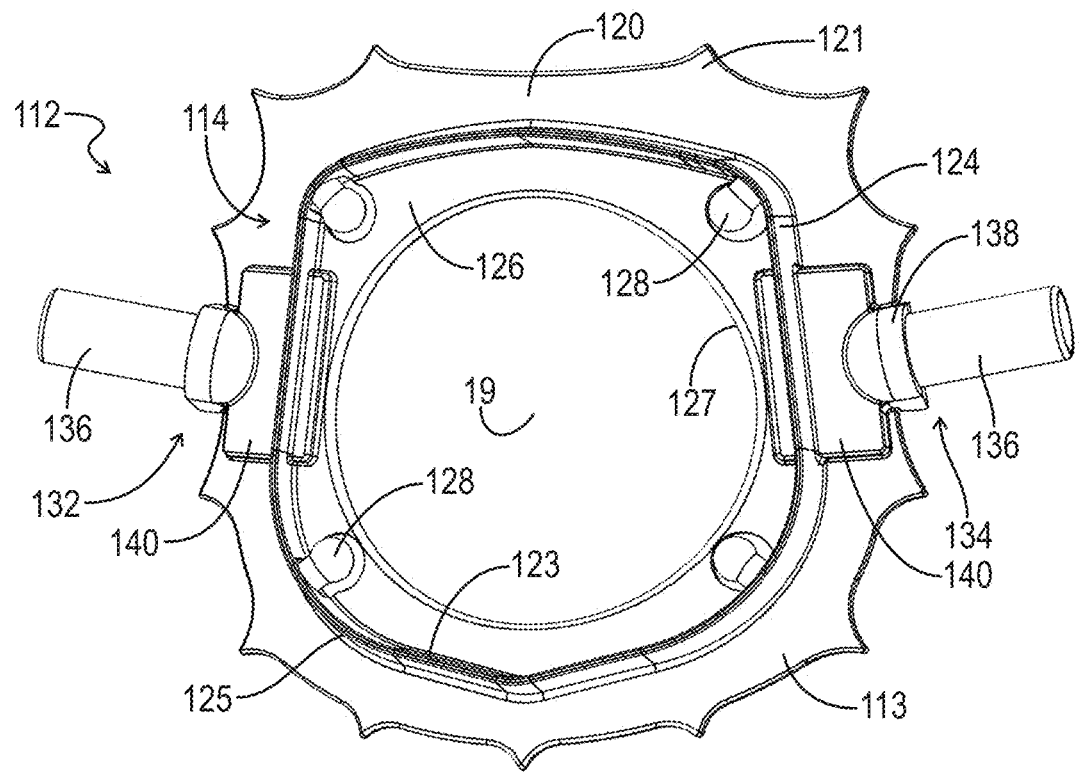
FIG. 19 is an isometric front view of another embodiment of the ring assembly.
Figure 20:
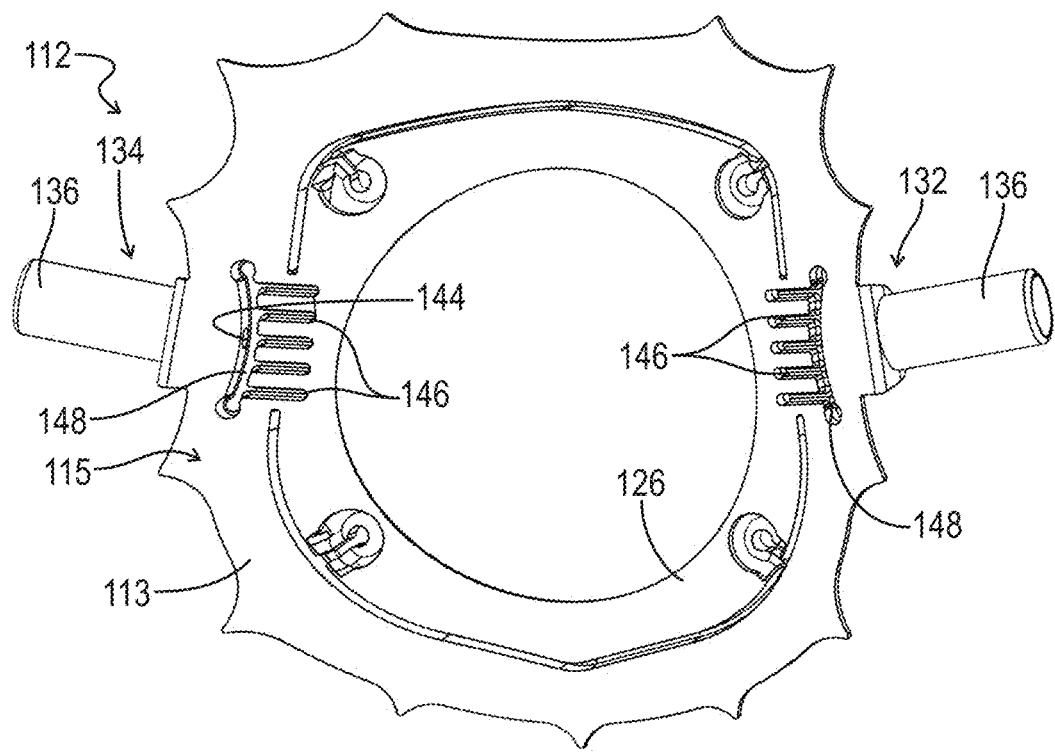
FIG. 20 is an isometric rear view of the ring assembly shown in FIG. 19.

FIGS. 19 and 20 illustrate another embodiment of the ring assembly 112 of the present invention, which is similar to ring assembly 12 in many respects, except that the frame 113 does not have a reduced width portion along its upper area 20, although upper area 120 is still contoured to extend over the upper lip of the patient without interfering with the nose or nostrils, and the middle portion of the upper area 120 is free of any tines. In addition, extension connectors 128 which are used to attach one or more flexible aerosol barrier extensions to the ring assembly 112, instead of being positioned on the outer wall surface 24 of collar 22 in ring assembly 12, are attached facing inwardly on the inner wall surface 123 of collar 124. Extension connectors 128 are also more globe-shaped than extension connectors 28, which are more candle-shaped. Another modification is that inner lip or ring 126 is substantially continuous or aligned with frame 113, rather than being connected to collar 24 in close proximity to the outer edge 25 of the collar 24. The inner lip or ring 126 therefore is not raised superiorly away from the patient as in ring assembly 12.

Nozzles 136 of suction ports 132 and 134 on ring assembly 112 are secured to a strengthening member 138 formed on the front or outer surface 114 of frame 113, which in turn is connected to a suction housing 140 also formed on surface 114. The suction housing 140 extends through collar 124 on to inner lip or ring 126, rather than being positioned underneath inner lip or ring 26 as in ring assembly 12. As shown in FIG. 20, a plurality of aligned branch channels 146 are formed in rear surface 115 of frame 113 in alignment with the suctions housings 140 and extend inwardly on to lip or rim 126. Branch channels 146 connect on their outermost end to a main channel 148 also formed in frame 113 on rear surface 115. A high-volume suction aperture 144 connects through an inner wall of the suction housings 140 into main channel 148. Aperture 144 is also in fluid communication with nozzle 136, such that each of the nozzles 136 is in direct fluid communication with the channels 146 and 148. In use, the ring assembly 112 is connected to a high velocity suction source such as source 100 described above, such that a powerful suction flow is generated in the high-volume suction aperture 144. The channels 146 and 148 provide an increased surface area on the inner surface 115 of the frame 113 and lip 126 in which the suction flow is generated, which distributes the suction circumferentially around the entire rear surface 115 of the dam frame 112, drawing aerosol particles expelled from the patient's mouth into the aperture 144 to be collected by the associated vacuum system. The curvature of the frame 113 is such that the channels 146 and 148 are not flush against the skin or face of the patient and by design will be in close proximity to the oral cavity. In use therefore the inner lip or ring 126 will follow the convex contours of the face in general, but will be relieved superiorly at least a small distance positioned away from the mouth and lips. The ring assembly 112 may also include posts or similar connectors to be mounted to the support mask and may be used either alone or in combination with the support mask.

Figure 21:
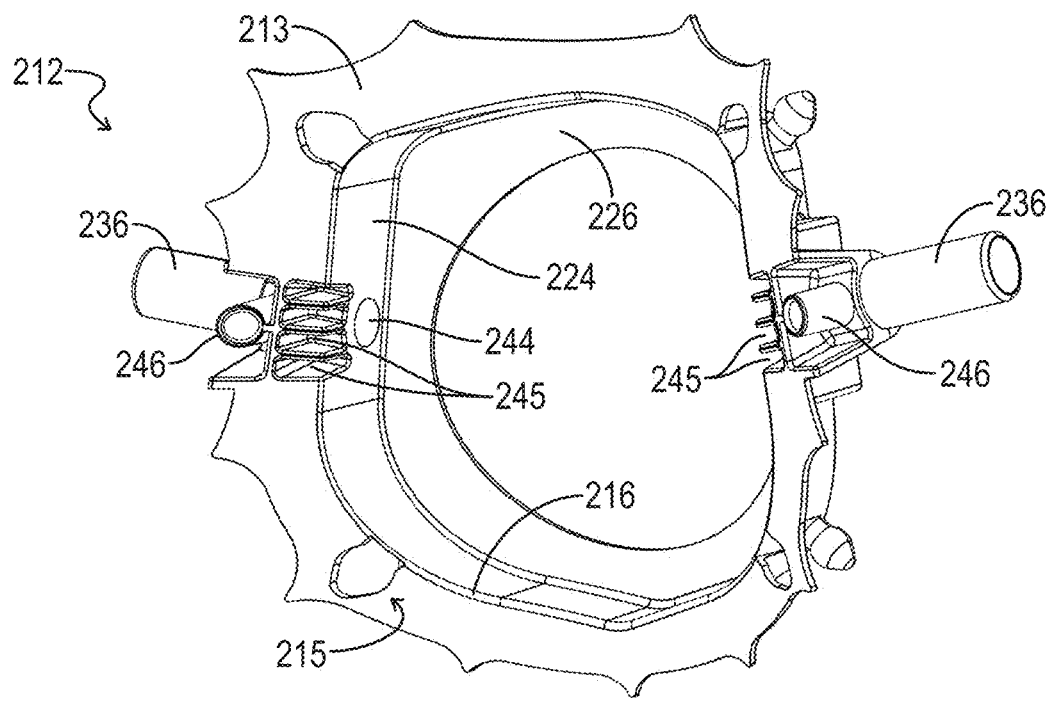
FIG. 21 is an isometric rear view of another embodiment of the ring assembly.

FIG. 21 illustrates another embodiment of the ring assembly 212, which is similar to ring assembly 12 in many respects, except that collar 224 is slightly wider than collar 24 on ring assembly 12, such that the inner rim or lip 226 is spaced superiorly a greater distance away from the patient's mouth or face. In addition, a plurality of aligned channels 245 are formed in rear surface 215 of the ring assembly 212 on frame 213 in a position beside sleeves 246. The channels 245 extend to inner edge 216, and also open on to collar 224. The channels 245 in collar 224 are also aligned with inner aperture 244 of the nozzles 236 which open on to the inner surface of the collar 224 at apertures 244. The aligned channels 245 aid in trapping aerosol particles under the frame 213 and in directing the particles towards the apertures 244.

Figure 22:
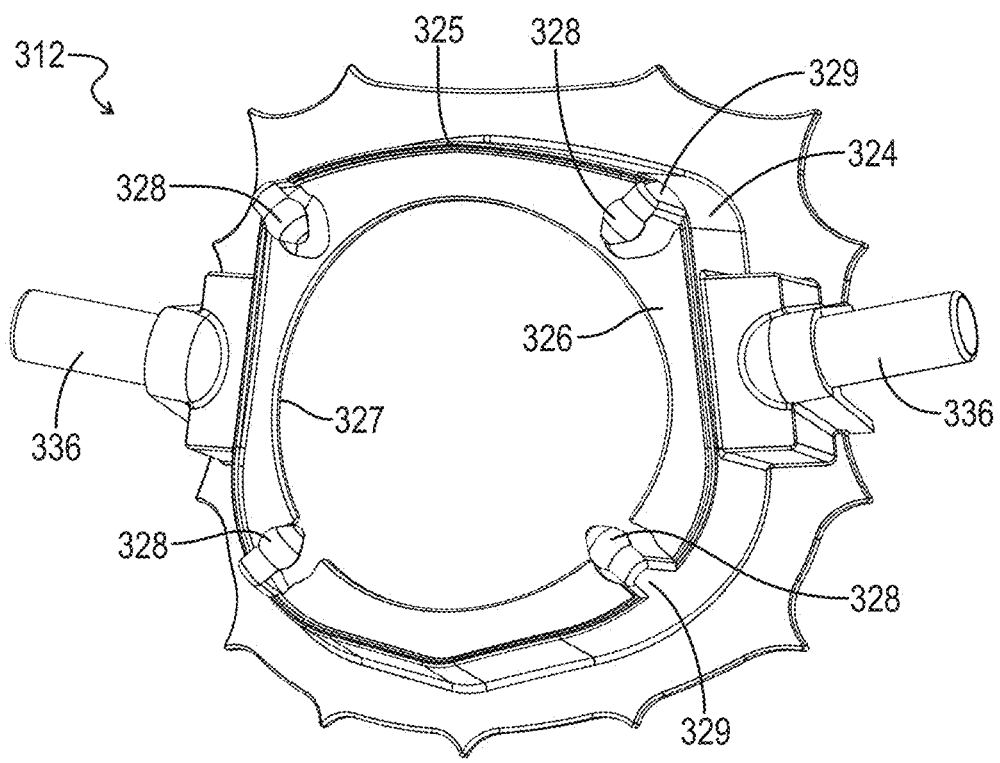
FIG. 22 is an isometric rear view of another embodiment of the ring assembly.

FIG. 22 illustrates another embodiment of the ring assembly 312, which is similar to ring assembly 12 in many respects, except that the plurality of connectors 328 are mounted on supports 329. Supports 329 extend upwardly from the outer rim 325 of the collar 324, and the connectors 328 are directed inwardly with respect to the ring assembly 312 and extend over inner lip or ring 326. The raised position of connectors 328 on supports 329 enables the connectors to be positioned facing inwardly, rather than being positioned on the outer surface of collar 24 as in ring assembly 12. Nozzles 336 are in the same position as in the previous embodiments.

Figure 23:
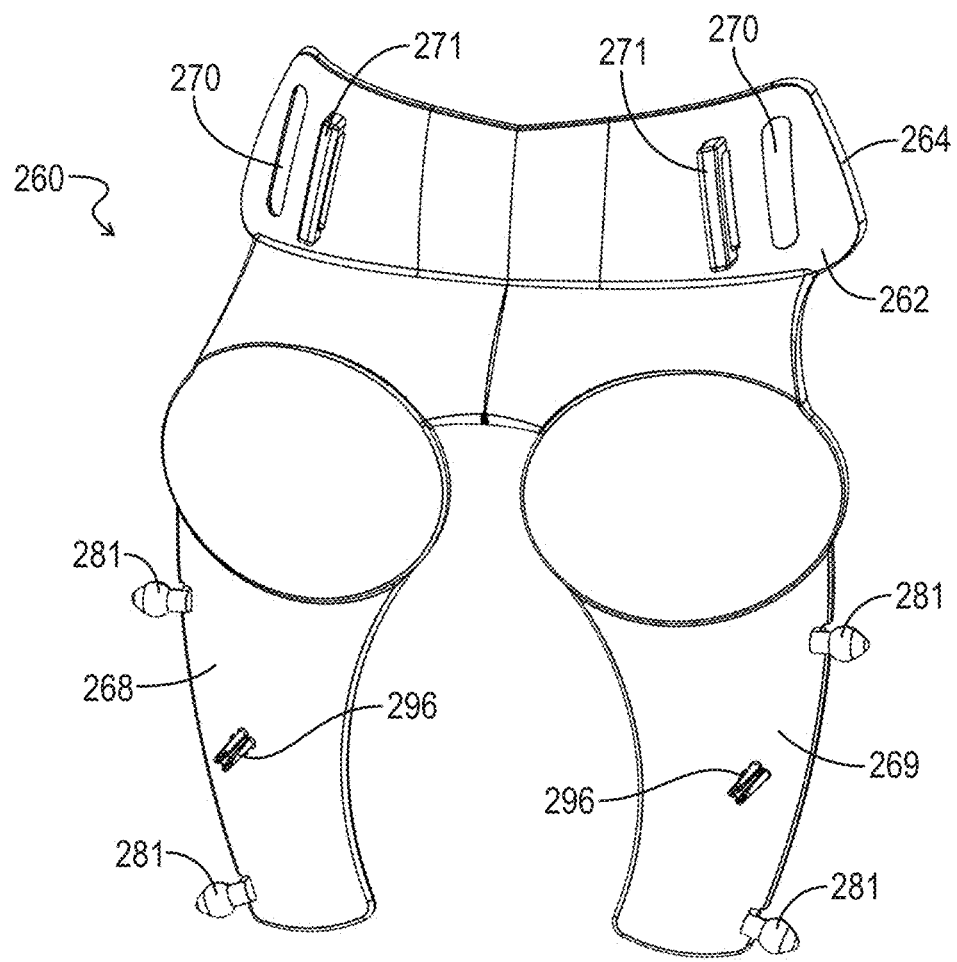
FIG. 23 is an isometric view of another embodiment of the support mask.

FIG. 23 illustrates another embodiment of the support mask 260, which is similar to the support mask 60 in many respects, except that inverted C-shaped tabs 271 are formed on anterior surface 262 of forehead covering region 264 in alignment with the slots 270. Tabs 271 are configured to receive a band or strap 72 extending underneath the tabs 271 which is also passed through the slots 270. In addition, support mask 260 does not contain suction ports 88 and 89 as in support mask 60, and therefore is designed primarily to be used in combination with the ring assembly 12 in accordance with embodiments of the present invention. In other embodiments, suction nozzles may be detachably mounted to the support mask which can be removed when the support mask is used in combination with the ring assembly or when the nozzles are not in use and may be attached when the support mask is used as a standalone device as described herein. For example, apertures may be provided in the cheek covering regions in which support members for the nozzles are coupled by a friction fit or other suitable attachment means. In addition, fittings 296 on cheek covering regions 268 and 269 of support mask 260 have an irregular outer surface rather than being formed as sleeves 96 on support mask 60.

In any of the alternate modes of use of the aerosol protection system 10, the inwardly directed suction nozzles provide a powerful suction around the oral cavity which draws aerosolized particles emitted from the patient's mouth into the nozzles. In addition, the overall structure of both the ring assembly and support mask inhibit aerosol particles from escaping into the operatory. The inwardly directed lip 26 on the ring assembly 12 reduces the size of the working area 19 of the system 10, and positioning the suction openings 44 under lip 26 facilitates provision of a negative pressure under the lip 26 when the suction source is activated. In addition, the flexible extensions 56 when secured to ring assembly or the support mask serve as an adjustable safety barrier between the dental professional and patient's oral cavity extending around and at least partially over the work area, further protecting those in the operatory against potentially infectious splatter and aerosols while also aiding in guiding or funneling the aerosols toward the suction apertures or source of suction.

Collar 22 on the ring assembly 12 provides some structural support for the base or end of the flexible extensions attached to the connectors, and aids in holding the extensions extending superiorly away from the patient and draped partially over the work area. It will be understood that a single flexible extension may be secured extending around the periphery of the work area, or two or more extensions each extending partially around the work area may be utilized. Additional flexible extensions may be positioned around the side edges of the ring assembly and support mask to reduce possible aerosol leakage in the small spaces between the patient's face and the underside of the ring assembly or frame, or between the frame and ring assembly, as deemed necessary by the dental professional. The flexible extensions are preferably disposable, may have different lengths, and may be shaped or cut using standard scissors to allow the operator the proper access needed to the operating field during the dental procedure. Periodic stiffening members may also be attached to or formed with the flexible extensions to aid in maintaining the extensions in a desired extended position, or the extensions may have a ribbed pattern. In another embodiment, a semirigid plastic extension formed of a polycarbonate or polyester (PET) film material may be attached concurrently with the flexible extensions 56 to the connectors on the ring assembly or mask, forming a somewhat more rigid shield extending superiorly away from the patient around the work area. In a further aspect, connectors may be provided on the underside of the collar or inner rim for attaching a light and/or camera to the ring assembly. The collar or rim may also be altered by the dental professional if needed to allow better access to the field of operation for a particular procedure using a large acrylic trimming bur/stone, similar to denture acrylic shaping burs/stones. The collar and rim on the ring assembly work in unison with the flexible extension as described herein to increase the power of the vacuum suction being utilized to remove aerosols, and to alter the trajectory of any remaining escaping aerosols into a lower arc that the plastic extension will likely catch. The inner perimeter of the work area is defined by the inner rim or ring, which may be continuous with the frame portion or joined to a forward lip or flange as in the embodiments herein. In ring assembly 12, the open ends 44 of the nozzles 36 are situated underneath the inner lip or ring 26, providing a funneling shelf that creates the adjustable mouth opening or aperture through which the operator has access. The ring assembly and support mask are reusable, sterilizable, easy to use, customizable and economical, and effectively contain aerosols. In a further aspect, the ring assembly may be connected to an external support arm such that the device is suspended from the arm, whereby the position of the support arm is adjusted to ensure that the device is maintained in a most useful position over the patient's mouth area, or to quickly move the device away from its use position if needed. In other embodiments, the support structure may have a different appearance while still serving the purpose of supporting the ring device in a stable position over the patient's mouth area.

The foregoing description has been presented for purposes of illustration and description and is not intended to be exhaustive or to limit the invention to the precise form disclosed. The descriptions were selected to explain the principles of the invention and their practical application to enable others skilled in the art to utilize the invention in various embodiments and various modifications as are suited to the particular use contemplated. Although particular constructions of the present invention have been shown and described, other alternative constructions will be apparent to those skilled in the art and are within the intended scope of the present invention.

What is claimed is:

1. A dental aerosol protection device comprising:
  a head-mountable face mask for protecting portions of a patient's face during a dental procedure having an anterior surface and a posterior surface, and including a forehead covering region, a brow covering region, eye covering regions, and cheek covering regions;
  wherein the posterior surface is contoured to conform to the face of the patient, the forehead covering region is adapted to directly engage with the patient's forehead, and the cheek covering regions extending from the eye covering regions on opposite sides of the patient's nose and mouth and each having an inner margin, an outer margin, and a lower margin dimensioned to extend at or below the corner of the patient's mouth;
  a ring assembly detachably securable to the face mask, the ring assembly having a front surface, a rear surface, and including a frame portion dimensioned to extend circumferentially around the oral cavity of the patient, a collar portion projecting outwardly from the frame portion, a lip portion having an inner edge defining a central opening in the ring assembly, a plurality of spaced apart extension connectors joined to the collar portion of the ring assembly, and one or more suction ports joined to the ring assembly each having a suction nozzle operably couplable on one end to a suction generating device and another end forming a suction aperture on the ring assembly; and
  one or more flexible extensions detachably connectable on an end to one or more of the spaced-apart connectors on the ring assembly with another end extending superiorly away from the front surface of the ring assembly;
  wherein the one or more flexible extensions act as a flexible side wall and a barrier to splatter and aerosols being emitted from the oral cavity of the patient, and wherein when a suction force is generated by the suction device a negative suction pressure is exerted circumferentially within the central opening bordered by the flexible extensions, drawing potentially harmful aerosolized particles into the suction nozzle.

2. The oral aerosol protection device of claim 1 additionally comprising at least one fastening component on the ring assembly, and at least one mating fastening component on the cheek covering regions of the face mask, wherein the ring assembly is securable to the face mask in a fixed position extending between the cheek covering regions.

3. The oral aerosol protection device of claim 2 in which the at least one mating fastening component of the face mask is a mounting post attached extending outwardly from the anterior surface of the cheek covering regions of the face mask, and the mating fastening component on the ring assembly is a sleeve, wherein the mounting post is insertable into the sleeve and secured in the sleeve by a friction fit.

4. The oral aerosol protection device of claim 1 wherein the lip portion of the ring assembly extends inwardly from the collar portion.

5. The oral aerosol protection device of claim 4 wherein the suction apertures on the ring assembly are located on an inner surface of the collar portion underneath the lip portion.

6. The oral aerosol protection device of claim 1 additionally comprising a plurality of tines spaced apart on an outer edge of the frame portion of the ring assembly for detachably securing a dental dam sheet to the frame portion.

7. The oral aerosol protection device of claim 1 wherein the facemask additionally comprises a suction nozzle mounted extendingly over the anterior surface of a cheek covering region of the face mask, the suction nozzle having an outer end configured to be operably coupled by a suction line with the suction generating device, and an inner end forming a suction aperture directed to provide a suction force along the inner margin of the cheek covering region.

8. The oral aerosol protection device of claim 7 additionally comprising one or more extension connectors joined to the cheek covering regions of the face mask.

9. The oral aerosol protection device of claim 8 wherein one or more of the flexible extensions is detachably securable to the extension connectors on the face mask in an orientation extending superiorly away from the anterior surface of the cheek covering regions, forming an enclosure around the periphery of the patient's oral cavity and providing a barrier against aerosols and splatter emitted from the patient's mouth, and wherein during application of the suction force in the suction nozzle of the cheek covering region of the facemask a negative suction pressure is exerted circumferentially around the periphery of the oral cavity bordered by the flexible extension, drawing aerosols emitted from the oral cavity into the suction nozzle.

10. The oral aerosol protection device of claim 9 in which the extension connectors on the face mask are positioned along the outer margin of the cheek covering regions.

11. The oral aerosol protection device of claim 1 wherein the brow covering region of the face mask extends downwardly and outwardly from a lower end of the forehead covering region such that the brow covering region and eye covering regions are spaced outwardly from the patient's face.

12. The oral aerosol protection device of claim 1 additionally comprising an adjustable strap connected to the forehead covering region of the face mask for securing around the patient's head.

13. The oral aerosol protection device of claim 1 wherein the flexible extensions are formed of a flexible plastic having an open-ended tubular configuration.

14. The oral aerosol protection device of claim 1 wherein the face mask is formed of a transparent or translucent plastic material.

15. An oral aerosol protection device for limiting dispersion of aerosolized particles during dental procedures comprising a patient interface securable to the head of a patient, and a ring assembly detachably securable to the patient interface and configured to be aligned with the patient's oral cavity, wherein the patient interface and ring assembly may be operably used either secured together or individually;
the patient interface forming a head-mountable structure including an anterior surface and a posterior surface, cheek covering regions configured to extend over opposite sides of the patient's nose and mouth to a position below the corner of the patient's mouth, a suction nozzle mounted to the cheek covering regions having an outer end configured to be operably coupled by a suction line to a suction generating device, and an inner end forming a suction aperture directed to provide a suction force along an inner margin of the cheek covering regions; and one or more extension connectors joined to the cheek covering regions;
the ring assembly including a frame dimensioned to extend circumferentially around the oral cavity of the patient, a collar projecting forwardly from the frame, an inwardly projecting lip having an inner edge defining a central opening in the ring assembly, a suction port attached to the frame having a suction nozzle configured to be operably coupled by a suction line to the suction generating device, a suction aperture opening on to the collar or rear surface of the frame, and a plurality of spaced-apart extension connectors attached to the collar; and
a flexible side wall extension detachably securable to the extension connectors on the patient interface or ring assembly, the flexible side wall extension configured to form an open-ended aerosol and splatter barrier around the patient's oral cavity;
wherein during application of a suction force generated by the suction generating device connected to at least one of the suction nozzles of the patient interface or ring assembly a negative suction pressure is generated around the periphery of the oral cavity bordered by the flexible side extension, drawing potentially harmful aerosols emitted from the oral cavity into the suction nozzle.

16. The oral aerosol collection device of claim 15 additionally comprising at least one fastening component on the ring assembly and at least one mating fastening component on the cheek covering regions of the patient interface, wherein the ring assembly is attachable to the patient interface in a fixed position extending between the cheek covering regions.

17. The oral aerosol collection device of claim 16 in which the collar of the ring assembly extends superiorly outwardly from an inner edge of the frame, and the inwardly projecting lip is connected to the collar at a spaced apart location from the inner edge of the frame.

18. The oral aerosol collection device of claim 17 in which the suction aperture of the suction nozzle of the ring assembly open on to an inner surface of the collar on an underside of the lip, forming a barrier which traps aerosol and splatter particles emitted by the patient underneath the lip, and wherein a high-volume suction at the suction apertures creates a circumferential negative pressure under the lip and funnels a flow of air towards the suction apertures.

19. The oral aerosol collection device of claim 18 in which the patient interface is a support mask having a forehead covering region configured to directly engage with the patient's forehead, and an adjustable strap connectable to the forehead covering region for securing the support mask to the patient's head.

20. The oral aerosol collection device of claim 19 in which a brow covering region is joined to the forehead covering region along a lower edge of the forehead covering region and is angled forwardly so as to protrude outwardly from the forehead covering region, eye covering regions joined to the brow covering region along a lower edge of the brow covering region, and wherein the check covering regions are joined to the eye covering regions along a lower edge of eye covering regions.

\* \* \* \* \*